US011857808B2

(12) United States Patent
Packer et al.

(10) Patent No.: US 11,857,808 B2
(45) Date of Patent: Jan. 2, 2024

(54) SYSTEM AND METHOD FOR CARBON PARTICLE THERAPY FOR TREATMENT OF CARDIAC ARRHYTHMIAS AND OTHER DISEASES

(71) Applicant: Mayo Foundation for Medical Education and Research, Rochester, MN (US)

(72) Inventors: Douglas L. Packer, Rochester, MN (US); Samuel J. Asirvatham, Rochester, MN (US); Suraj Kapa, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 496 days.

(21) Appl. No.: 16/641,917

(22) PCT Filed: Aug. 31, 2018

(86) PCT No.: PCT/US2018/049114
§ 371 (c)(1),
(2) Date: Feb. 25, 2020

(87) PCT Pub. No.: WO2019/046732
PCT Pub. Date: Mar. 7, 2019

(65) Prior Publication Data
US 2020/0179722 A1 Jun. 11, 2020

Related U.S. Application Data

(60) Provisional application No. 62/552,614, filed on Aug. 31, 2017.

(51) Int. Cl.
| | | |
|---|---|---|
| *G06T 7/149* | (2017.01) | |
| *A61N 5/10* | (2006.01) | |
| *G06T 7/00* | (2017.01) | |
| *G06T 11/00* | (2006.01) | |

(52) U.S. Cl.
CPC ......... *A61N 5/1049* (2013.01); *A61N 5/1039* (2013.01); *G06T 7/0012* (2013.01); *G06T 7/149* (2017.01); *G06T 11/005* (2013.01); A61N 2005/1058 (2013.01); A61N 2005/1087 (2013.01); A61N 2005/1098 (2013.01); G06T 2207/10081 (2013.01); G06T 2207/10088 (2013.01); G06T 2207/20116 (2013.01); G06T 2207/30048 (2013.01)

(58) Field of Classification Search
CPC .................. G06T 7/0012; G06T 7/149; G06T 2207/20116; G06T 2207/30016; G06T 2207/30048; A61N 5/1037; A61N 5/1049; A61N 2005/1058; A61N 2005/1087; A61N 2005/1089; A61N 2005/109
See application file for complete search history.

(56) References Cited

U.S. PATENT DOCUMENTS

| | | | |
|---|---|---|---|
| 7,322,929 B2 | 1/2008 | Lovoi | 600/3 |
| 8,784,290 B2 | 7/2014 | Sumanaweera et al. | 600/1 |
| 9,320,916 B2 | 4/2016 | Sumanaweera et al. | A61N 5/1037 |
| 11,406,845 B2 | 8/2022 | Robinson et al. ... | A61N 5/1039 |
| 2004/0162596 A1 | 8/2004 | Altshuler et al. | 607/88 |
| 2004/0260142 A1 | 12/2004 | Lovoi | 600/1 |
| 2007/0041499 A1 | 2/2007 | Lu et al. | 378/65 |
| 2008/0023644 A1 | 1/2008 | Pedroni | 250/400 |
| 2008/0221382 A1 | 9/2008 | Karshafian et al. | 600/2 |
| 2009/0180589 A1* | 7/2009 | Wang et al. | A61N 5/1082 378/65 |
| 2010/0301235 A1 | 12/2010 | Bert et al. | 250/492.3 |
| 2011/0107270 A1 | 5/2011 | Wang et al. | 715/850 |
| 2012/0014501 A1* | 1/2012 | Pelc et al. | A61N 5/1049 378/9 |
| 2012/0241635 A1 | 9/2012 | Luechtenborg et al. | 250/389 |
| 2013/0211482 A1 | 8/2013 | Piiponen | A61N 5/01 |
| 2013/0237822 A1 | 9/2013 | Gross et al. | 600/439 |
| 2016/0035108 A1* | 2/2016 | Yu et al. | A61B 34/20 382/131 |
| 2017/0014642 A1 | 1/2017 | An | A61N 5/1039 |
| 2017/0203123 A1* | 7/2017 | Requardt et al. | G06T 7/0012 |

FOREIGN PATENT DOCUMENTS

| | | | |
|---|---|---|---|
| WO | 2012154219 A2 | 11/2012 | A61B 18/18 |
| WO | 2013034709 A1 | 3/2013 | A61N 5/10 |
| WO | 2016193929 A2 | 12/2016 | A61N 1/32 |

OTHER PUBLICATIONS

Poulsen P R, et al. 2014 Kilovoltage intrafraction motion monitoring and target dose reconstruction for stereotactic volumetric modulated arc therapy of tumors in the liver Radiother Oncol 111 424-30.
Prall, M., et al. "Treatment of arrhythmias by external charged particle beams: a Langendorff feasibility study." Biomedical Engineering/Biomedizinische Technik 60.2 (2015): 147-156.
Raaymakers B W, et al. 2009 Integrating a 1.5 T MRI scanner with a 6 MV accelerator: proof of concept Phys. Med. Biol 54 N229-N37.
Ravkilde T, et al. 2013 Time-resolved dose distributions to moving targets during volumetric modulated arc therapy with and without dynamic MLC tracking Med. Phys 40 111723.
Rettmann, M. E., et al. "Analysis of left atrial respiratory and cardiac motion for cardiac ablation therapy." Medical Imaging 2015: Image-Guided Procedures, Robotic Interventions, and Modeling. vol. 9415. International Society for Optics and Photonics, 2015.

(Continued)

*Primary Examiner* — Andrew W Johns
(74) *Attorney, Agent, or Firm* — Quarles & Brady LLP

(57) ABSTRACT

Particle or hadron therapy is used on abnormal tissue using carbon atoms, protons, or helium atoms run through a linear accelerator and then directed at the target in the body. This can be used to treat, for example, atrial fibrillation, ventricular tachycardia, hypertension, seizures, gastrointestinal maladies, etc. Contouring and gating may be used to account for cardiac and respiratory motion, helping reduce collateral damage.

52 Claims, 24 Drawing Sheets

(56) References Cited

OTHER PUBLICATIONS

Rettmann, M. E., et al. "Centerline Tracking for Quantification of Reverse Structural Remodeling of the Pulmonary Veins Following Cardiac Ablation Therapy." Academic radiology 19.11 (2012): 1332-1344.

Richter C, et al. 2016 First clinical application of a prompt gamma based in vivo proton range verification system Radiother Oncol 118.2 (2016): 232-237.

Richter D, et al. 2013 Upgrade and benchmarking of a 4D treatment planning system for scanned ion beam therapy Med. Phys 40 051722.

Richter D, et al. 2014 Four-dimensional patient dose reconstruction for scanned ion beam therapy of moving liver tumors Int J Radiat Oncol Biol Phys 89 175-81.

Richter D, et al. 2014 Residual motion mitigation in scanned carbon ion beam therapy of liver tumors using enlarged pencil beam overlap Radiother. Oncol 113 290-5.

Richter, D, et al. "ECG-based 4D-dose reconstruction of cardiac arrhythmia ablation with carbon ion beams: application in a porcine model." Physics in Medicine & Biology 62.17 (Aug. 4, 2017): 6869.

Roujol S, et al. 2013 Characterization of respiratory and cardiac motion from electro-anatomical mapping data for improved fusion of MRI to left ventricular electrograms PLoS One 8 e78852.

Scandurra D, et al. 2016 Assessing the quality of proton PBS treatment delivery using machine log files: comprehensive analysis of clinical treatments delivered at PSI Gantry 2 Phys Med Biol 61 1171-81.

Schardt D, et al. 2010 Heavy-ion tumor therapy: Physical and radiobiological benefits Reviews of Modern Physics 82 383.

Shackleford J A, et al. 2010 On developing B-spline registration algorithms for multi-core processors Physics in Medicine and Biology 55 6329-51.

Sharma A, et al. New non-invasive therapy for cardiac arrhythmias using stereotactic radiosurgery: initial feasibility testing. Heart Rhythm. 2007;68. Abstract.

Sharma A, et al. Non-invasive ablation of the left superior pulmonary vein-left atrial junction using stereotactic focused radiation. Circulation. 2007;116:489. Abstract.

Sharma A, et al. Non-invasive approach to myocardial ablation: pathology of stereotactic robot targeted high energy x-ray lesions at potential arrhythmia sites. Heart Rhythm. 2008;67. Abstract.

Sharma A, et al. Noninvasive stereotactic radiosurgery (CyberHeart) for creation of ablation lesions in the atrium. Heart Rhythm. 2010;7:802-810. doi: 10.1016/j.hrthm.2010.02.010.

Soejima K, et al. Catheter ablation in patients with multiple and unstable ventricular tachycardias after myocardial infarction: short ablation lines guided by reentry circuit isthmuses and sinus rhythm mapping. Circulation. 2001;104:664-669.

Soejima K, et al. Endocardial and epicardial radiofrequency ablation of ventricular tachycardia associated with dilated cardiomyopathy: the importance of low-voltage scars. J Am Coll Cardiol. 2004;43:1834-1842. doi: 10.1016/j.acc.2004.01.029.

Sosnovik, D. E., et al. "Magnetic nanoparticles for MR imaging: agents, techniques and cardiovascular applications." Basic research in cardiology 103.2 (2008): 122-130.

Suleiman M, et al. The noncoronary cusp as a site for successful ablation of accessory pathways: Electrogram characteristics in three cases. J Cardiovasc Electrophsiol. 2010.

Takami M, et al. Effect of left atrial ablation process and strategy on microemboli formation during irrigated radiofrequency catheter ablation in an in vivo model. Circ Arrhythm Electrophysiol. 2016;9:e003226. doi: 10.1161/CIRCEP.115.003226.

Uhl M, et al. 2014 High control rate in patients with chondrosarcoma of the skull base after carbon ion therapy: first report of long-term results Cancer 120 1579-85.

Yu L, et al. Autonomic denervation with magnetic nanoparticles. Circulation. 2010;122:2653-2659.

Zei PC et al. "Ablative radiotherapy as a noninvasive alternative to catheter ablation for cardiac arrhythmias." Current cardiology reports 19.9 (Jul. 27, 2017): 79.

Zei PC et al. First-in-man treatment of atrial fibrillation using cardiac radiosurgery. Heart Rhythm. 2016;5. Abstract.

Achenbach S, et al. 2000 Noninvasive coronary angiography by retrospectively ECG gated multislice spiral CT Circulation 102 2823-8.

Asirvatham SJ. Advances in catheter ablation: a burning trail! Indian Heart Journal.2011;379-85.

Beddar A S, et al. 2007 Correlation between internal fiducial tumor motion and external marker motion for liver tumors imaged with 4D-CT Int. J. Radiat. Oncol. Biol. Phys 67 630-8.

Bert C et al. 2011 Motion in radiotherapy: particle therapy Phys. Med. Biol 56 R113-R44.

Blanck O, et al. 2014 Dose-escalation study for cardiac radiosurgery in a porcine model Int J Radiat Oncol Biol Phys 89 590-8.

Bode F, et al. 2015 Pulmonary vein isolation by radiosurgery: implications for noninvasive treatment of atrial fibrillation Europace 17 1868-74.

Calkins H, et al. 2012 HRS/ EHRA/ECAS expert consensus statement on catheter and surgical ablation of atrial fibrillation: recommendations for patient selection, procedural techniques, patient management and follow-up, definitions, endpoints, and research trial design. Heart Rhythm. 2012;9:632-696.e21. doi: 10.1016/j.hrthm.2011.12.016.

Cappato R, et al. Updated worldwide survey on the methods, efficacy, and safety of catheter ablation for human atrial fibrillation. Circ Arrhythm Electrophysiol. 2010;3:32-38. doi: 10.1161/CIRCEP.109.859116.

Chaudhri N, et al. 2012 Clinical Implementation of Gating and Dose Verification with Scanned Ion Beams at HIT. In: Med Phys AAPM, pp. 3780-3781.

Constantinescu, A. et al. Catheter-Free Ablation of Atrial Fibrillation: Further Planning Studies in Patient Data Using a Scanned Carbon Ion Beam for Pulmonary Vein Isolation. MP04-02. Hearth Rhythm, vol. 11, No. 5, May Supplement 2014.

Constantinescu, A., et al. "Planning studies for non-invasive isolation of the pulmonary veins with a scanned carbon ion beam." Heart Rhythm 10 (2013): S33.

Constantinescu, A., et al. "Treatment planning studies in patient data with scanned carbon ion beams for catheter-free ablation of atrial fibrillation." Journal of cardiovascular electrophysiology 27.3 (2016): 335-344.

Deisher, A. et al. Catheter-Free Ablation With External Photon Radiation: Treatment Planning, Delivery Considerations, and Correlation of Effects With Delivered Dose. Heart Rhythm, vol. 12, No. 5, May Supplement 2015.

Del Carpio Munoz F; et al. Three-dimensional mapping of cardiac arrhythmias: what do the colors really mean? Circ Arrhythm Electrophysiol. Dec. 2010; 3(6)e6-11.

Deneke T, et al. Silent cerebral events/ lesions related to atrial fibrillation ablation: a clinical review. J Cardiovasc lectrophysiol. 2015;26:455-463. doi: 10.1111/jce.12608.

Dickfeld T, et al. MRI-guided ventricular tachycardia ablation: integration of late gadolinium-enhanced 3D scar in patients with implantable cardioverter-defibrillators. Circ Arrhythm Electrophysiol. 2011;4:172-184. doi: 10.1161/CIRCEP.110.958744.

Dinov B, et al. Early referral for ablation of scarrelated ventricular tachycardia is associated with improved acute and ong-term outcomes: results from the Heart Center of Leipzig ventricular tachycardia registry. Circ Arrhythm Electrophysiol. 2014,7:1144-1151. doi: 10.1161/CIRCEP.114.001953.

Fishbein MC, et al. Early phase acute myocardial infarct size quantification: validation of the triphenyl tetrazolium chloride tissue enzyme staining technique. Am Heart J. 1981; 101:593-600.

Franceschi F, et al. Hislopathological effects and evolution of transvenous β-radiation applications in right and left atria: an animal study. Europace. 2012;14:745-751. doi: 10.1093/europace/eur351.

Ge J, et al. 2013 Planning 4-dimensional computed tomography (4DCT) cannot adequately represent daily intrafractional motion of abdominal tumors Int J Radiat Oncol Biol Phys 85 999-1005.

(56) References Cited

OTHER PUBLICATIONS

Gerstenfeld EP. Recurrent ventricular tachycardia after catheter ablation in post-infarct cardiomyopathy: "failure" of ablation or progression of the substrate? J Am Coll Cardiol. 2013;61:74-76. doi: 10.1016/j.jacc.2012.07.057.
Graeff C et al., 2012, Motion mitigation in intensity modulated particle therapy by internal target volumes covering range changes Med. Phys 39 6004-13.
Grimm J, et al. Dose tolerance limits and dose volume histogram evaluation for stereotactic body radiotherapy. J Appl Clin Med Phys. 2011;12:3368.
Guerra PG, et al. Beta-radiation for the creation of linear lesions in the canine atrium. Circulation. 2004;110:911-914. doi: 10.1161/01.CIR.0000139865.39885.03.
Haberer T, et al. 1993 Magnetic scanning system for heavy ion therapy Nucl. Instrum. Meth. A 330 296-305.
Hartman J, et al. 2015 Dosimetric feasibility of intensity modulated proton therapy in a transverse magnetic field of 1.5 T Phys Med Biol 60 5955-69
International Searching Authority, International Search Report and Written Opinion for application PCT/US2018/049114, dated Nov. 21, 2018.
Kachelriess M, et al. 2000 ECG-correlated image reconstruction from subsecond multi-slice spiral CT scans of the heart Med Phys 27 1881-902.
Keall P J, et al. 2014 The first clinical implementation of electromagnetic transponder-guided MLC tracking Med Phys 41 020702.
Keall P J, et al. 2015 The first clinical treatment with kilovoltage intrafraction monitoring (KIM): a real-time image guidance method Med. Phys 42 354-8.
Kumar S, et al. 2012 Effect of respiration on catheter-tissue contact force during ablation of atrial arrhythmias Heart Rhythm 9 1041-7 e1.
Kuntz J, et al. 2010 Fully automated intrinsic respiratory and cardiac gating for small animal CT Phys Med Biol 55 2069-85.
Lehmann HI, et al. Delineation of Target Locations and Organs at Risk for Particle Beam Therapy: Atlas for Extracorporeal CT-Based Ablation of Cardiac Tissue. Heart Rhythm, vol. 11, No. 5, May Supplement 2014.
Lehmann HI, et al. "External arrhythmia ablation using photon beams: ablation of the atrioventricular junction in an intact animal model." Circulation: Arrhythmia and Electrophysiology 10.4 (Apr. 2017): e004304.
Lehmann HI, et al. "Feasibility study on cardiac arrhythmia ablation using high-energy heavy ion beams." Scientific reports 6 (2016): 38895.
Lehmann HI, et al. "In-Beam PET Verification of Catheter-free Arrhythmia Ablation by Scanned Carbon-12 Ion Beam Irradiation." Circulation 132.suppl_3 (2015): A12443-A12443.
Lehmann HI, et al. Atrioventricular node ablation in Langendorffperfused porcine hearts using carbon ion particle therapy: methods and an in vivo feasibility investigation for catheter-free ablation of cardiac arrhythmias. Circ Arrhythm Electrophysiol. 2015,8:429-438. doi: 10.1161/ CIRCEP.114.002436.
Lehmann HI, et al. Biophysics of Tissue Ablation in Catheter-Free Ablation With Carbon Ion Beams. May 2016 vol. 13, Issue 5, Supplement, pp. S1-S96.
Lin M H, et al. 2012 4D patient dose reconstruction using online measured EPID cine images for lung SBRT treatment validation Med. Phys 39 5949-58.
Maguire P, et al. 2011 Cardiac radiosurgery (CyberHeart) for treatment of arrhythmia: physiologic and histopathologic correlation in the porcine model Cureus 3 e32.
Ng, J. et al. Mapping of Dominant Activation Directions in a Canine Rapid Atrial Pacing Model of Atrial Fibrillation. Heart Rhythm Session. May 12, 2017.
Okumura Y, et al. Three-dimensional ultrasound for image-guided mapping and intervention: methods, quantitative validation, and clinical feasibility of a novel multimodality image mapping system. Circ Arrhythm Electrophysiol. 2008;1:110-119. doi: 10.1161/ CIRCEP. 108.769935.
Ortmaier T, et al. 2005 Motion estimation in beating heart surgery IEEE Trans Biomed Eng 52 1729-40.
Pan J et al. 1985 A real-time QRS detection algorithm IEEE Trans Biomed Eng 32 230-6.
Pérez-Castellano N, et al.. Pathological effects of pulmonary vein beta-radiation in a swine model. J Cardiovasc Electrophysiol. 2006; 17:662-669. doi: 10.1111/j.1540-8167.2006.00462.x.
Peulen H, et al. Mid-ventilation based PTV margins in stereotactic body radiotherapy (SBRT): a clinical evaluation. Radiother Oncol. 2014;110:511-516. doi: 10.1016/j.radonc.2014.01.010.
Pfanner F, et al. 2013 Monitoring internal organ motion with continuous wave radar in CT Med Phys 40 091915.
Pfanner F, et al. 2014 Monitoring cardiac motion in CT using a continuous wave radar embedded in the patient table Med Phys 41 081908.
Piersanti L, et al. 2014 Measurement of charged particle yields from PMMA irradiated by a 220 MeV/u (12)C beam Phys Med Biol 59 1857-72.
Poulsen P R, et al. 2012 A method of dose reconstruction for moving targets compatible with dynamic treatments Med. Phys 39 6237-46.

* cited by examiner

SYSTEM AND METHOD FOR CARBON PARTICLE THERAPY FOR TREATMENT OF CARDIAC ARRHYTHMIAS AND OTHER DISEASES

CROSS-REFERENCE TO RELATED APPLICATIONS

This application represents the national stage entry of International Application No. PCT/US2018/049114, filed on Aug. 31, 2018, which claims the benefit of U.S. Provisional Patent Application Ser. No. 62/552,614, filed on Aug. 31, 2017, and entitled "System and Method for Carbon Particle Therapy for Treatment of Cardiac Arrhythmias and Other Diseases," which is herein incorporated by reference in its entirety.

STATEMENT REGARDING FEDERALLY SPONSORED RESEARCH

N/A.

FIELD OF THE DISCLOSURE

This document concerns an invention relating generally to the use of particle or hadron therapy to target specific tissues, and more specifically, to delivery of accelerated atoms and protons into, for example, the heart to more deeply penetrate the tissue and reach the particular source of abnormal heart rhythms despite tissue movement.

BACKGROUND

Cardiac arrhythmias, a condition in which the heart beats irregularly, can lead to strokes, infarctions, and sudden cardiac arrest. Cardiac arrhythmias are disturbances of the coordinated heart rhythm that may originate from the upper (atria) and lower (ventricles) chambers of the heart. The most common sustained arrhythmia that originates from the atria is atrial fibrillation (AF). In the Unites States, there are nearly five million patients who have atrial fibrillation, which is a highly chaotic, abnormal heart rhythm arising in the upper chambers of the heart. There are 200,000 new patients presenting with this abnormal rhythm on a yearly basis. Another serious arrhythmia is ventricular tachycardia. This occurs in the lower pumping chambers and is usually related to heart failure or a prior heart attack. Around 300,000 patients die suddenly each year due to different types of this ventricular arrhythmia.

Many of these patients are treated with antiarrhythmic drugs. If drugs are ineffective, a switch is made to conventional ablation. With ablation, catheters are inserted into the heart to thermally treat the areas responsible for the chaotic rhythm. Clinically available methods for ablation rely on local thermal damage to the targeted arrhythmogenic substrate, which could be nodal tissue like the AV node, atrial tissue, or ventricular myocardial tissue. In order to achieve this, heating or cooling of the tissue is effected via electrode-tipped catheters placed in the heart. A prerequisite for such ablation is contact on the internal or epicardial surface of the heart with the catheter and cardiac tissue since the maximal thermal effects occur at the interface between tissue and electrode.

While ablation has been a critical addition to the treatment armamentarium, the catheter-based methods currently available have limited success with both of these arrhythmias. The success rate for use of ablation to treat atrial fibrillation is 70% over the course of one year, and at five years, the success has dropped down below 50%. The success rate is even lower if the patients have underlying disease, such as a prior heart attack or heart failure. Catheter-based means of attempting to ablate ventricular tachycardia have success rates somewhere between 20 and 70%, and most patients require an additional ablation. Furthermore, most of these patients also require an implantable cardioverter defibrillator (ICD) pacemaker device. These are quite expensive, and up to 70% of patients with such defibrillators will have repeat episodes of an arrhythmia, which can either be life threatening, or require another ablation.

Cardiac ablation without catheters, using external beam sources such as microwave, where an antenna or equivalent is required for generation of thermal injury, has been tried with limited success. Targeted noncatheter ablation with high temporal and spatial resolution is not possible because of cardiac motion from contractility superadded to translational motion from, e.g., respiration and patient movement. This has led to significant complications, including damage to blood vessels leading to the heart, stroke, heart attacks, perforation of heart muscle causing bleeding sufficient to require open heart surgery, as well as damage to surrounding organs such as the esophagus, the diaphragm including the nerves activating that set of breathing muscles, and other possibilities damaging heart valves. External beam sources thus also require an internal catheter or electrode-like element to reduce collateral damage, as an internal catheter can serve as a real-time landmark to mimic, and thus compensate for, cardiac movement. Prior systems thus do not provide for targeted ablation without catheters, and the accompanying drawbacks.

What are needed are innovative techniques that address some or all of the safety and effectiveness issues of external beam therapy to allow for more successful treatment of patients with, for example, life-threatening arrhythmias.

SUMMARY OF THE PRESENT DISCLOSURE

In example embodiments, particle or hadron therapy is used to ablate abnormal heart rhythms. Atomic particles, such as carbon atoms, protons, or helium atoms, for example, may be run through a linear accelerator to accelerate them towards the speed of light. If directed at the heart, the atoms could be used to reach the source of abnormal heart rhythms. This approach can be used to treat, for example, atrial fibrillation and ventricular tachycardia, the latter of which often occurs around heart attack scars, making it difficult to deliver energy sufficient to penetrate the scar and eliminate the tachycardia. Delivery of accelerated atomic particles into the chest could more deeply penetrate tissue to deliver higher levels of energy. The accelerated atomic particles can be highly effective in creating tissue lesions sufficient enough to eliminate abnormal heart rhythms, but could also be safer for patients, avoiding organ damage that occurs with prior catheter-based ablation in patients. In certain implementations, contouring may be used to account for cardiac and respiratory motion, helping reduce collateral damage. The disclosed techniques are applicable to non-cardiac applications as well, such as for treatment of hypertension, seizures, gastrointestinal maladies, etc. The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

DETAILED DESCRIPTION OF THE PRESENT DISCLOSURE

Figure 1:
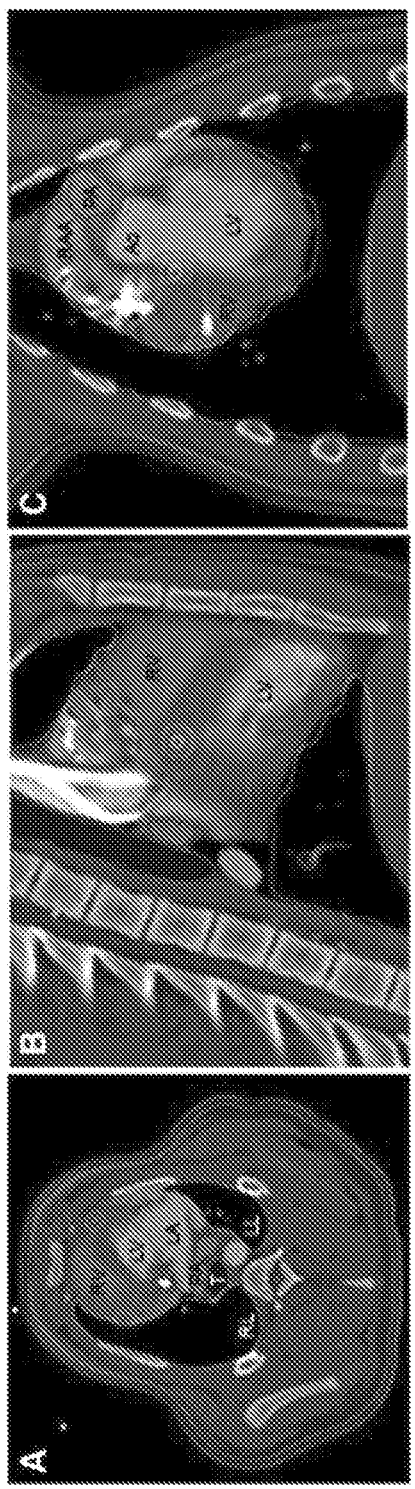
FIG. 1 shows contouring outcome for ablation of the atrioventricular junction in 3 planes of the cardiac phase-averaged computed tomographic (CT) scan: A, Axial (B) sagittal, and (C) coronal views, in accordance with one or more non-limiting example embodiments. The ablation target contour (clinical target volume [CTV]) is depicted in green and was the average of 2 physicians' contours during 10 cardiac phases. The enhanced target contour, covering the amplitude of cardiac motion is shown in light blue (internal target volume [ITV]). Finally, the final target volume (planning target volume [PTV]) is shown in magenta. Yellow=lungs; orange=trachea; blue=pulmonary arteries; red=left coronary arteries; green=right coronary artery; light green=skin; and dark blue=spinal canal. Note that coronary arteries are enhanced by a 5-mm margin to form protected risk volume [PRV]. By limiting the dose to the PRV in the optimizer, the dose to the coronary arteries is robust to positional uncertainties.

Treatment of cardiac arrhythmias and other diseases using an external radiation source for ablation of cardiac tissue may require taking into account motion (e.g. of dynamic tissues such as the heart or lungs) in order to ensure that the radiation is delivered to the appropriate location in the anatomy at the appropriate times and in the appropriate quantities. In some embodiments, catheters may be used to provide electrical information, or images, or location information of the heart during a treatment procedure. In various embodiments, focused photonic therapy can be accomplished without catheters, where imaging may be acquired prior to a radiation therapy treatment or images may be acquired during a treatment in order to provide guidance for the external radiation therapy system to accurately deliver therapy to the desired location in a highly focused and predicable manner. Appropriate real-time adjustment to cardiac respiratory and translational movement may be accomplished via imaging with phase contouring and gating of cardiac movement in the images to the energy source. External ablation and external mapping for correlation with ablation enable co-relating map and ablation efficacy so as to minimize collateral damage, as will be further discussed.

"Gating," sometimes referred to as triggering, is the process where a radiation treatment or an imaging system will deliver therapy or acquire images inside only a specified time window corresponding to a particular event or signal.

For cardiac-gated radiation therapy, a radiation beam may only be turned on to treat a subject when the heart is in a particular phase of the cardiac cycle in order to ensure that the area being treated is in the same location for each treatment dose, or fraction.

"Contouring" is the process of identifying and selecting a region or specific anatomy in an image. At a basic level, contouring may be outlining an organ in an image or a series of images to enable rapid identification of the organ. In a radiation therapy system, contouring may be used to follow critical targets trough a treatment cycle or fraction, minimizing or otherwise reducing the effect of motion on beam delivery For some clinical applications, the use of in-the-body catheters, either endocardial or epicardial, has not been sufficient to provide satisfactory results in all cases. Here, the use of multiple catheters such as both in endocardial and epicardial space, simultaneously or sequentially, has been tried with suboptimal success for ablation of mid-myocardial tissue. Implementations of the present disclosure not only can allow the spatial resolution in the beating heart to target cardiac and noncardiac tissue, but additionally phase contouring of the epi-f and endocardial surface separately allows for the targeting of specific regions, including hitherto inaccessible regions of cardiac tissue.

In example implementations, an internal electrode, an injected electrode, a catheter-like element, or an injected source of catheter or electrode-like particles including magnetic and ionizable micro and nanoparticles at the target site, may optionally be used to maximize the effects of external radiation. Injectable electrodes may be used so that the particulate beam can stimulate more reliably the area of injection, for example, into the skeletal muscle or subcutaneous patch and, in addition, to focus thermal injury to desired structures preferentially rather than the noninjected site. Small/nanoparticulate ionizable and possibly metallic injectates can be used for a similar purpose, such as into the arterial circulation, to focus energy delivery into the myocardium rather than surrounding structures and the blood pool where coagulation may occur.

That is, although the disclosed approaches can be used, for example, for in-heart catheterless ablation of targeted tissue, some implementations of the disclosure may use, for example, adjunctive catheters with circuitry and electromagnetic navigation tied into the energy delivery source to maximize cardiac registration and local therapy for some applications, such as for remodeling neural tissue that may be in close proximity to sensitive vasculature or conduction tissue.

Percutaneous catheters are presently the standard standalone method for cardiac mapping and ablation (see Asirvatham S J. Advances in catheter ablation: a burning trail! Indian Heart Journal. 2011, 63(4):379-385. Suleiman M, Brady P A, Asirvatham S J, Friedman P A, Munger T M. The noncoronary cusp as a site for successful ablation of accessory pathways: Electrogram characteristics in three cases. J Cardiovasc Electrophsiol. 2010, 22:203-209). In example implementations, the combined use of percutaneous, pericardial, subdural, per venous, and per subcutaneous placement of electrodes for sensing, stimulation, and focusing energy delivery lies in the simultaneous and concurrent use of external beam radiation at the time of stimulation and mapping. Thus, total energy delivered may be optimized by exact knowledge of termination of arrhythmia and detailed three-dimensional electroanatomic maps, which are in real time tagged via the synchronized electrical trigger between these two systems so as to deliver energy at the exact site and for the optimal duration to treat the pathological substrate. (Background may be found in: Del Carpio Munoz F; Buescher T L; Asirvatham S J. Three-dimensional mapping of cardiac arrhythmias: what do the colors really mean? Circ Arrhythm Electrophysiol. 2010 December; 3(6)e6-e11.)

As will now be further discussed, when the target (such as the heart) is in motion, contouring may be used to follow critical targets trough a treatment cycle, minimizing or otherwise reducing the effect of motion on beam delivery. Cyclical patterns of motion may be used to aid the targeting of cardiac tissue to be ablated, and avoidance of critical surrounding tissue to be left untreated. Also to be discussed is identifying and minimizing the entrance effect of leading edge Bragg peaks, minimizing risk to organs from parcel delivery, using phase tools for phase analysis, establishing the acute endpoint of hadron therapy delivery, denitrifying non-cardiac targets for particle therapy (including, but not limited to, seizures, left atrial appendage (LAA) occlusion, treatment of renal artery nerves causing hypertension, and creating antibodies and other molecular targets that can be activated using a particle beam to enhance effects with tissue activation instead of just tissue destruction).

Figure 20:
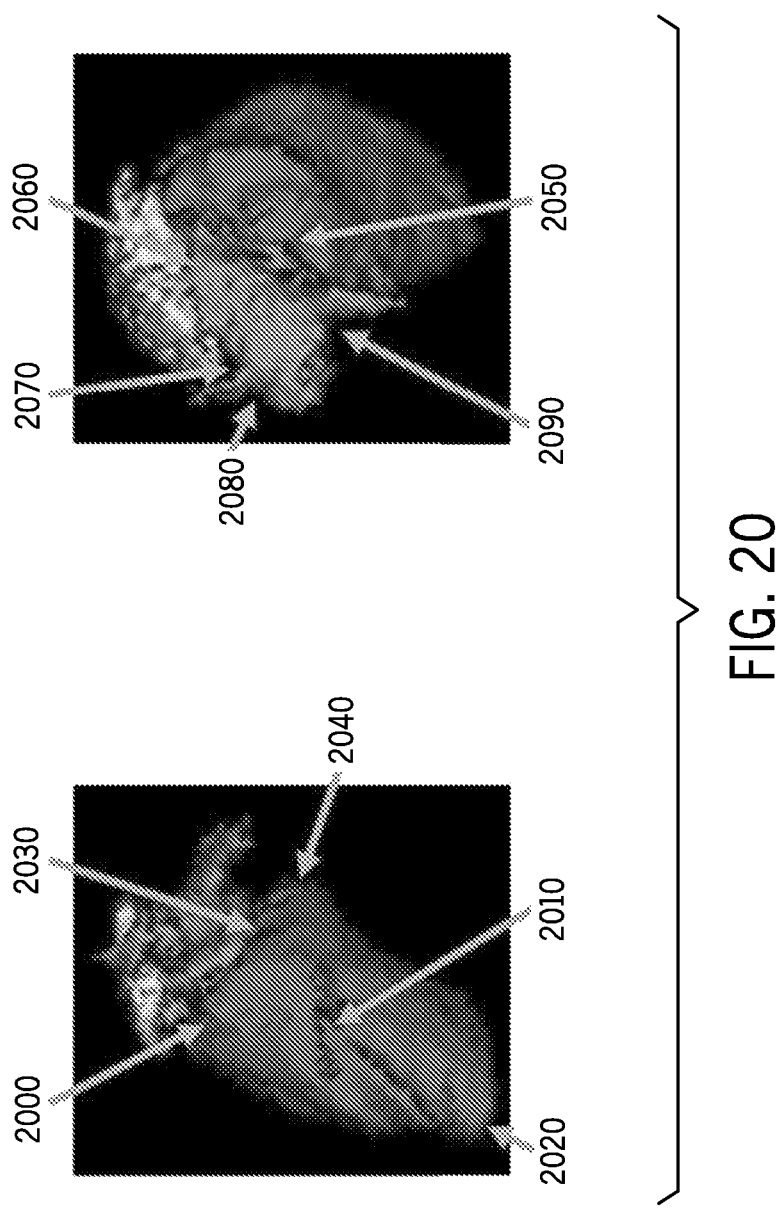
FIG. 20 is an image of a heart with anatomic locations identified which, in one configuration, may be used to compensate for cardiac motion when administering radiation therapy.

Referring to FIG. 20, one configuration for compensation of cardiac motion to ensure precise targeting may take the form of using anatomic landmarks during imaging. In one example, 10 landmarks may be tracked for a heart, including 5 in the left atrium and 5 in the left ventricle. The left ventricle, left atrium, and left atrial appendage may be segmented at each phase of the cardiac cycle using a 3D volume segmentation tool, such as in the Analyze 12.0 software, and time-volume curves may be computed. Ten anatomic landmarks distributed across the left ventricle and the left atrium may be identified across phases of the cardiac cycle. In the left ventricle, endocardial locations near the anterior papillary muscle (APM) 2000, posterior papillary muscle (PPM) 2010, left ventricular apex (LVA) 2020, mitral valve on left side (LVMV) 2030, and left aortic valve (LVAV) 2040 may be identified; in the left atrium, endocardial locations near the mitral valve (LAMV) 2050, the left atrial appendage (LAA) 2060, left superior pulmonary vein (LSPV) 2070, right superior pulmonary vein (RSPV) 2080, and inferior pulmonary vein (IPV) 2090 may be identified as shown in FIG. 20. Landmarks may be distributed across the chambers and may be chosen such that they could be reliably identified across all phases of the cardiac cycle. Motion trajectories may be computed using curve smoothing followed by a 3D curve spline fitting algorithm. In addition, the maximum displacement in each of the x, y, and z directions may be computed for each landmark.

Figure 21A:
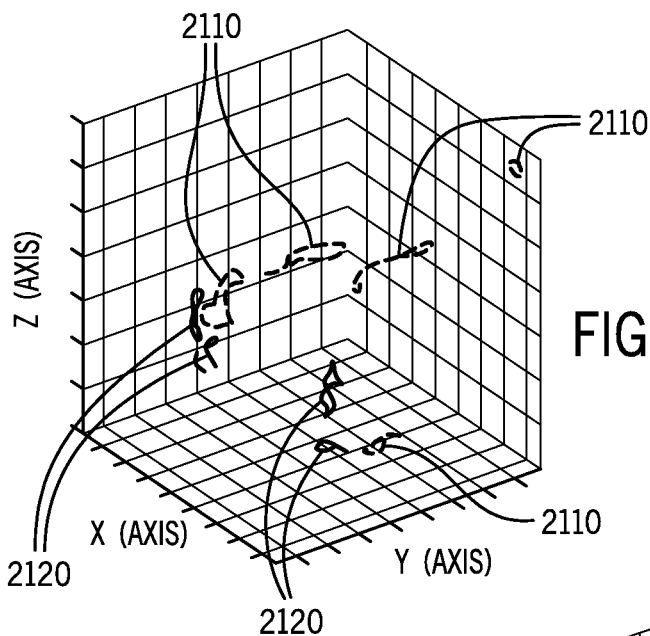
FIGS. 21A, 21B, and 21C are 3D trajectory maps of the anatomic locations from FIG. 20. 100381
Figure 21B:
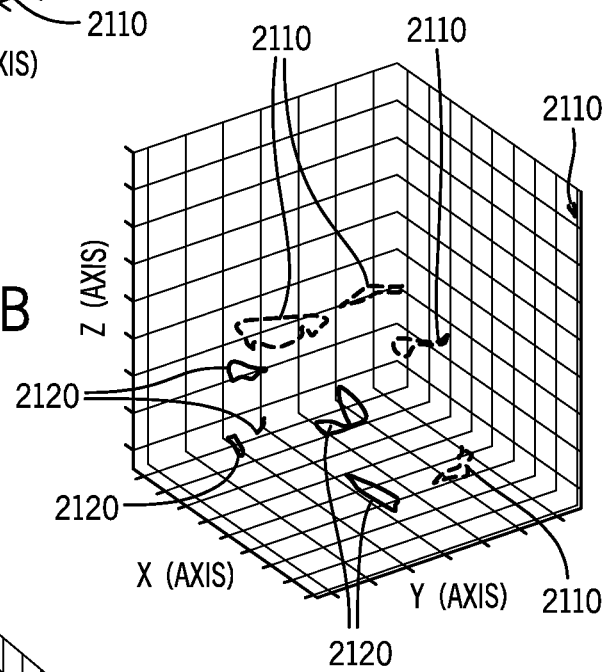
Figure 21C:
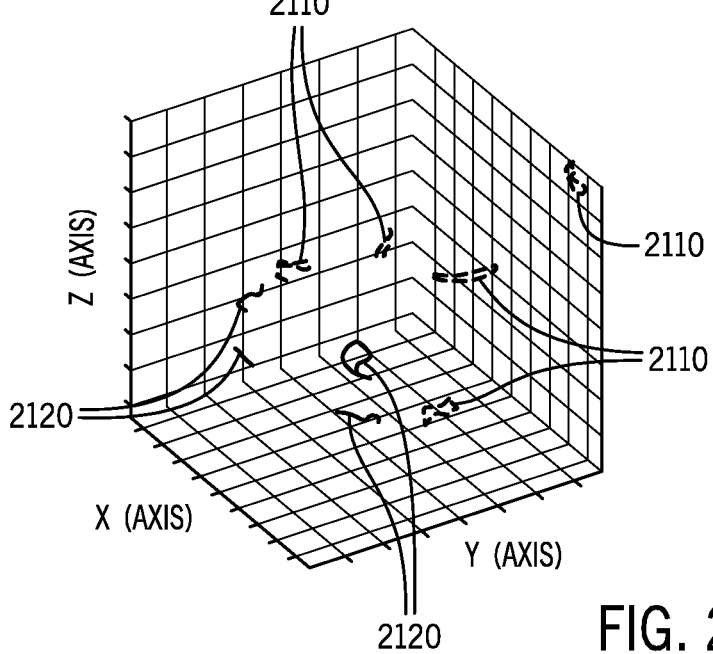

Referring to FIGS. 21A, 21B, and 21C, plots of 3D curve trajectories for the 10 tracked anatomic landmarks shown in FIG. 20 are depicted for 3 example hearts with the left ventricular landmarks 2010 and the left atrial landmarks 2020 shown.

Figure 22B:
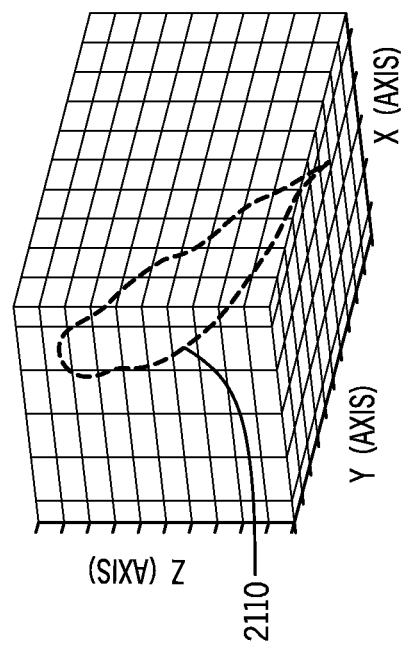
FIGS. 22A, 22B, 22C, and 22D are close up views of selected anatomic locations from FIGS. 21A, 21B and 21C showing variation among cardiac locations.
Figure 22D:
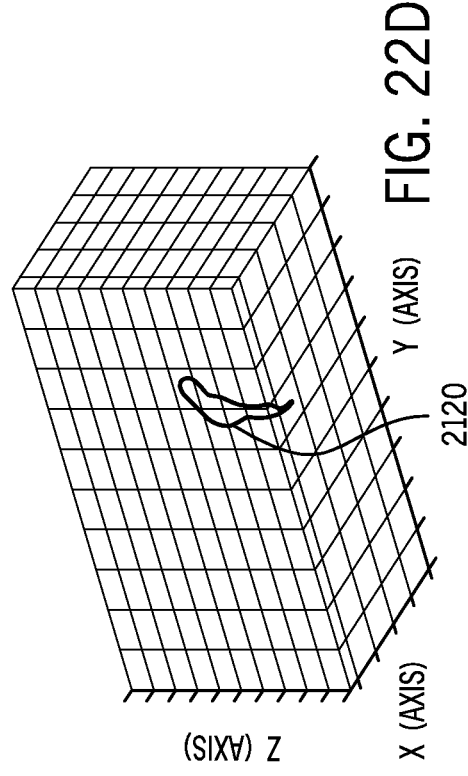
Figure 22A:
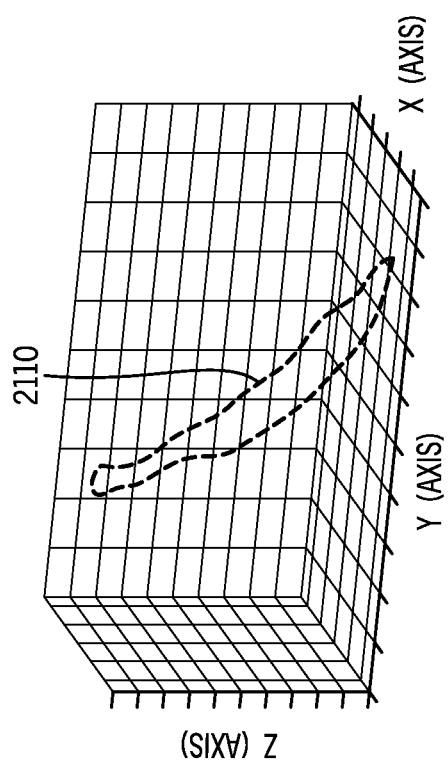
Figure 22C:
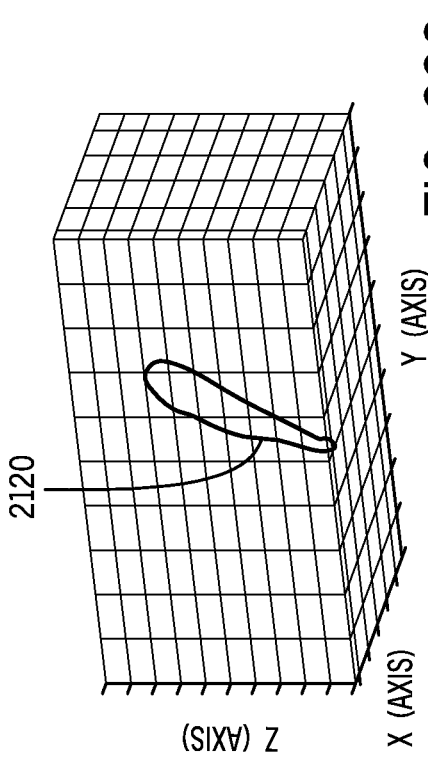

Referring to FIGS. 22A, 22B, 22C and 22D, a close up view of the 3D trajectories from FIGS. 21A, 21B, and 21C are shown for 4 individual landmarks. FIG. 22A depicts an APM, FIG. 22B depicts a PPM, FIG. 22C depicts a LAA, and FIG. 22D depicts an IPV. The figures indicate that a significant variation in motion trajectories exists across the various anatomic landmarks. In some configurations, the left ventricular landmarks demonstrate a larger magnitude of motion than those in the left atrium.

In some configurations, 3D cardiac motion across the left atrium and left ventricle of the heart may be quantified using multi-phase computed tomography datasets. Since there is the possibility for significant variation in 3D motion trajectories across different anatomic locations, detailed motion models are necessary for precise targeting of cardiac structures in external beam ablation therapy. In one example in the left atrium, total displacement was on the order of 5 to 6 mm in each of the x, y, and z dimensions. Left atrial thickness may range from 1.9 to 3.1 mm. Cardiac motion will need to be at least partially compensated in order for an external beam ablation approach to accurately target the left atrium. While the left ventricle is thicker, ranging from 0.9 to 1.5 cm between end systole and end diastole, its motion displacement may also larger, such as ranging from approximately 7 mm in the x direction and z direction to almost 10 mm in the y direction. Motion compensation may also be needed in the left ventricle in order to avoid collateral damage to surrounding tissue. Motion analysis may be valuable for quantification of cardiac motion as well as serving as a ground truth dataset for the validation of computational motion models.

In various embodiments, phase difference structural contouring provides optimal targeting with the particle beam, minimizes collateral damage, and serves as feedback for energy delivery.

In certain embodiments, the phase contouring itself may be done in two steps. In the first step, pre-procedural imaging (CT, MRI, PET, etc.) and use of ultrasound to tag specific tissues or structures based on its imaging, refractory, diffraction, and scatter characteristics along with its movement. This provides for tissue identification and labeling. Thus, rather than imaging an organ per se, specific structures with imaging and motion characteristics are identified. If we refer to such characterized structures as tissue time domains (TTDs), then these TTDs may be in a specific organ, across organs, or just part of a specific organ.

In certain iterations, multiple imaging sources, including those listed above, may be used to achieve successful phase contouring. First, sequential images may be obtained throughout a cardiac cycle and tagged to phases of the electrocardiogram such as the p-wave when present, peak QRS complex in multiple leads, and QRS and t-wave in multiple leads.

Specific cardiac structures with unique and differentiating movement with the cardiac cycle may then be tracked in by a motion sensing algorithm. To do this, the aortic, pulmonary, mitral, and tricuspid valve tip and endocardial base, endocardial apex, epicardial coronary artery and veins, epicardial base, epicardial apex, pulmonary veins, tip and base of atrial appendage, lateral and medial extents of vena cavae, and coronary sinus ostium may be labeled and movement tracked through the cardiac cycle. Machine learning may then be facilitated by the algorithm by inputting multiple cardiac cycles where the electrocardiogram is used as a reference and changes from one cardiac cycle through the other are either used to reject a particular cardiac cycle or to correct for the labeled moving part to differentiate it from noise or artifact. This complete endo, epi, and valve tissue contouring can provide precise input and real-time tracking of the photonic beam and other external beam source to allow effective energy delivery to the targeted tissue.

Figure 11A:
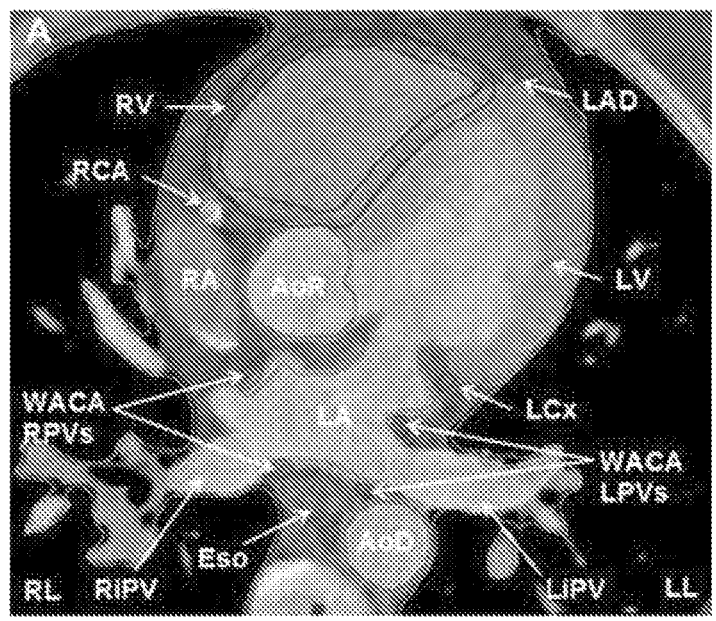
FIG. 11A provides an index beat example of manual description of relevant tissue regions (i.e., labeling), according to one or more embodiments. As labeled: RV—right ventricle; LAD—left anterior descending coronary artery; LV—left ventricle; LCx—left circumflex coronary artery; WACA—wide area circumferential ablation; LPVs—left pulmonary veins; LIPV—left inferior pulmonary vein; LL—left lung; AoD—ascending aorta; AoR—aorta; LA—left atrium; Eso—esophagus; RIPV—right inferior pulmonary vein; RL—right lung; RPV—right pulmonary vein; and RA—right atrium; RCA—right coronary artery.
Figure 11B:
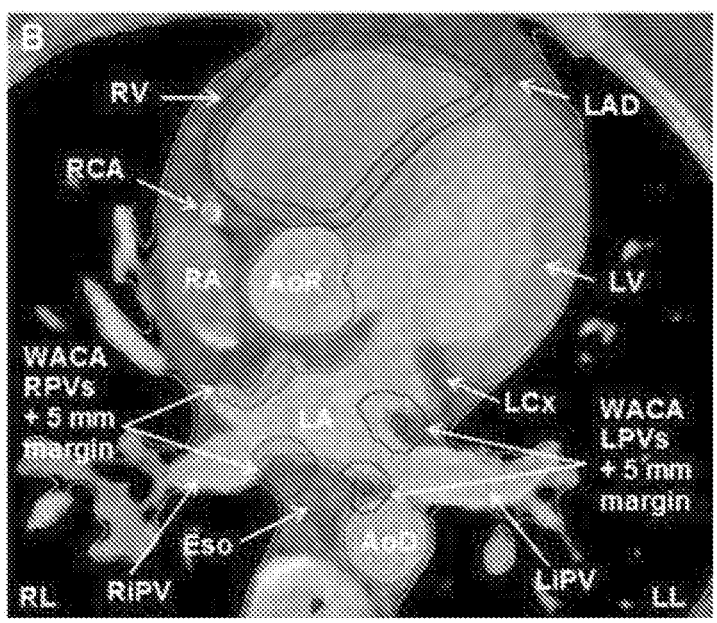
FIG. 11B provides an index beat example of manual description of relevant tissue regions (i.e., labeling), according to one or more embodiments. Labels correspond with labels of FIG. 11A. Close proximity of structures that are sensitive and in which injury could be catastrophic, such as the LAD lying in close proximity to structures that require ablation such as the LV, emphasizes the specific need for implementations of the present disclosure that allow for targeted contouring, motion sensitivity, and specific energy delivery.
Figure 12A:
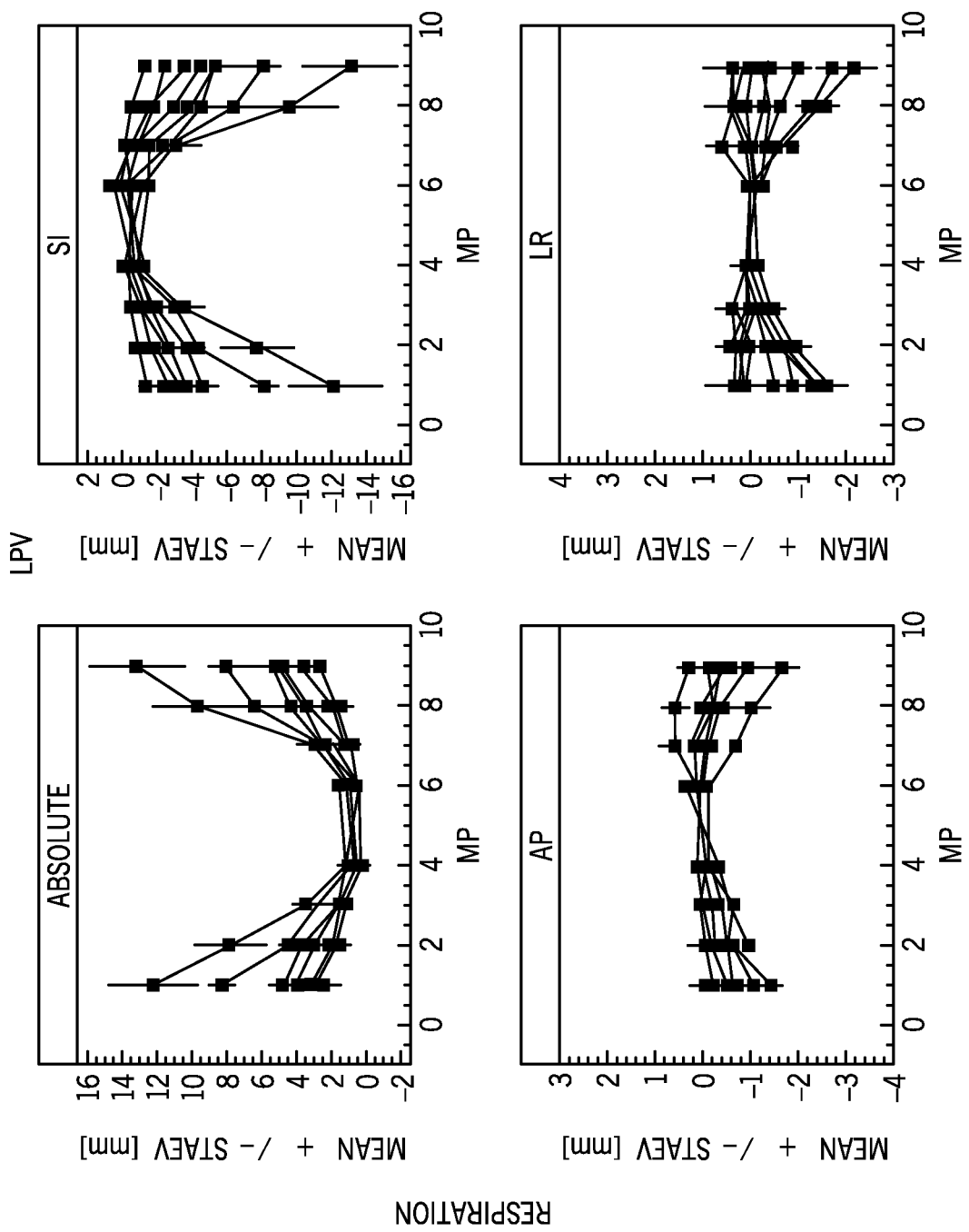
FIG. 12A illustrates performing deformable image registration to create a voxel to voxel map between reference and motion phases, according to one or more example embodiments. Illustrated is appropriate tracking of energy delivery with motion associated with respiration and contraction and relaxation of the heart (heartbeat). LPV corresponds with left pulmonary vein.
Figure 12B:
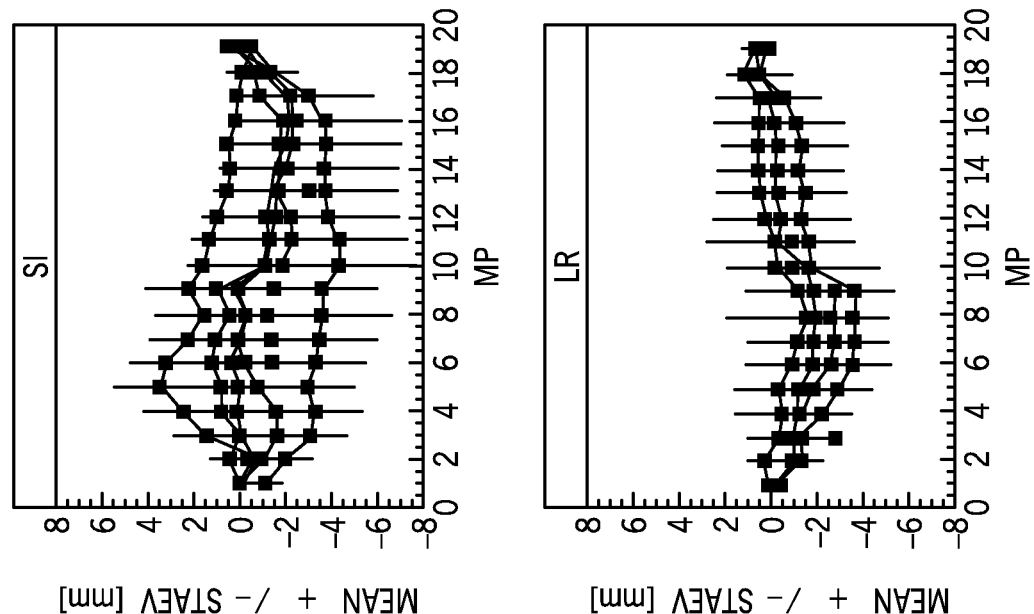
FIG. 12B illustrates performing deformable image registration to create a voxel to voxel map between reference and motion phases, according to one or more example embodiments. Illustrated is appropriate tracking of energy delivery with motion associated with respiration and contraction and relaxation of the heart (heartbeat). LPV corresponds with left pulmonary vein.
Figure 12B:
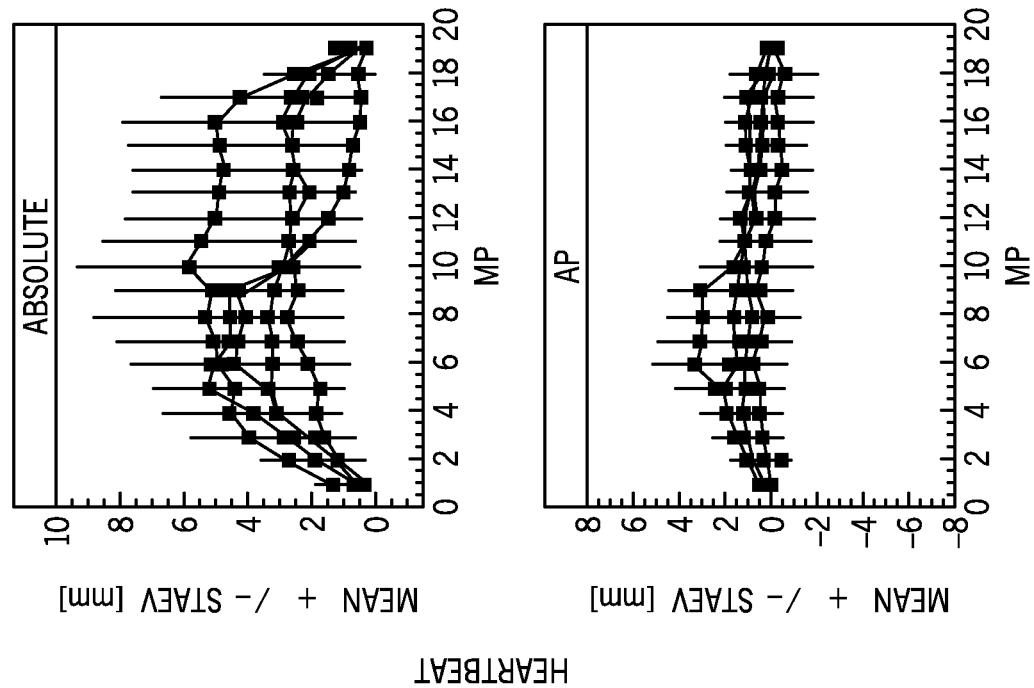
Figure 13A:
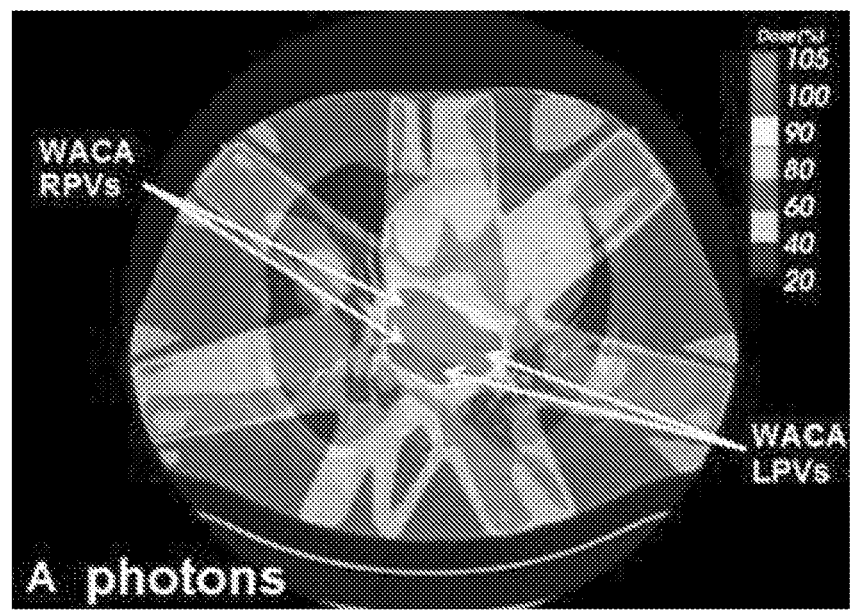
FIG. 13A provides an example focused Bragg peak with photons, according to one or more embodiments. As labeled, WACA corresponds with wide area circumferential ablation, RPV corresponds with right pulmonary vein, and LPV corresponds with left pulmonary vein. Illustrated are methods that facilitate focusing an enhanced delivery of energy at specific targeted sites, in this instance, the wall of the left atrium around the pulmonary vein (WACA).
Figure 13B:
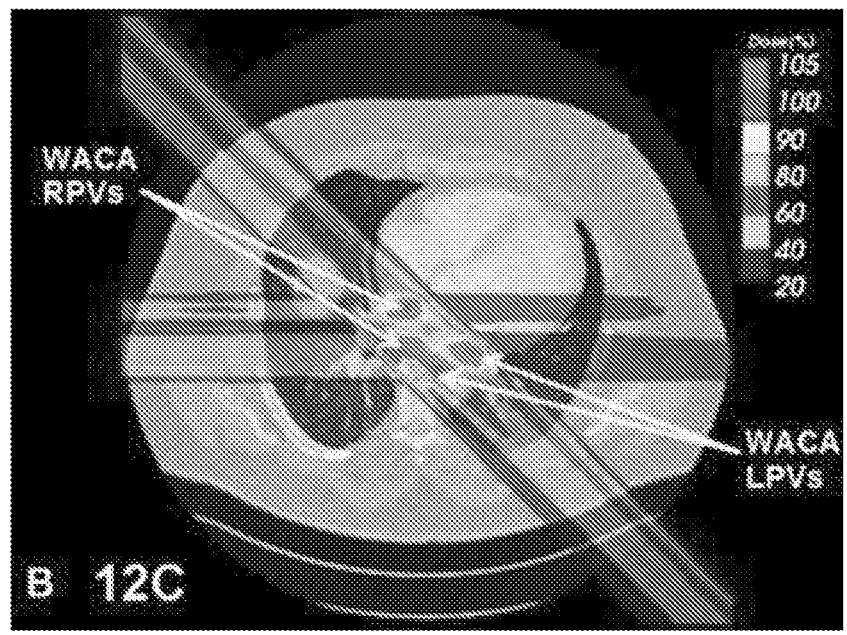
FIG. 13B provides an example focused Bragg peak with carbon-12 ($^{12}C$), according to one or more embodiments. As labeled, WACA corresponds with wide area circumferential ablation, RPV corresponds with right pulmonary vein, and LPV corresponds with left pulmonary vein. Illustrated are methods that facilitate focusing an enhanced delivery of energy at specific targeted sites, in this instance, the wall of the left atrium around the pulmonary vein (WACA).
Figure 14A:
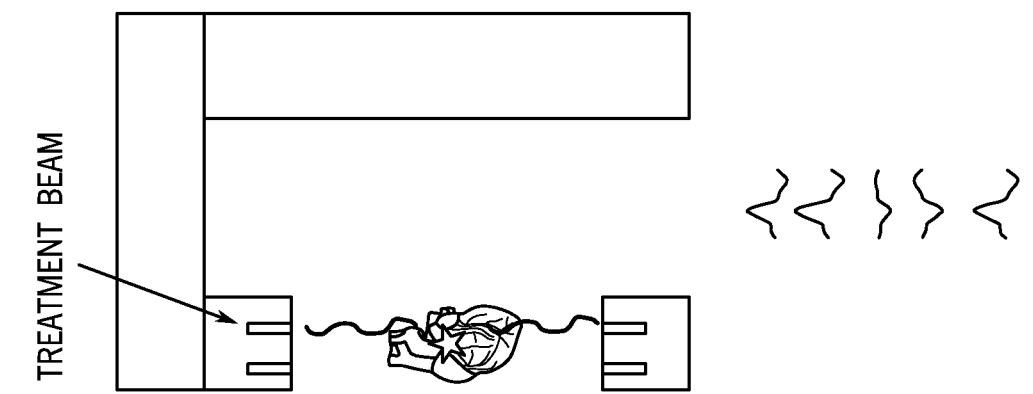
FIG. 14A depicts an example first stimulating beam stimulating tissue, according to one or more embodiments. Acceptance due to "pace map" indicates beams are aligned to same point, and rejection due to difference in "pace map" indicates beams are not aligned. Illustrated are spatially separate beams that may be pulsatile and not necessarily parallel as depicted in this figure. The stimulating beam, in a manner akin to direct electrical stimulation of the heart, may be used to perform diagnostic tests, induce cardiac arrhythmias, and mimic origin of cardiac arrhythmia (pace mapping).
Figure 14B:
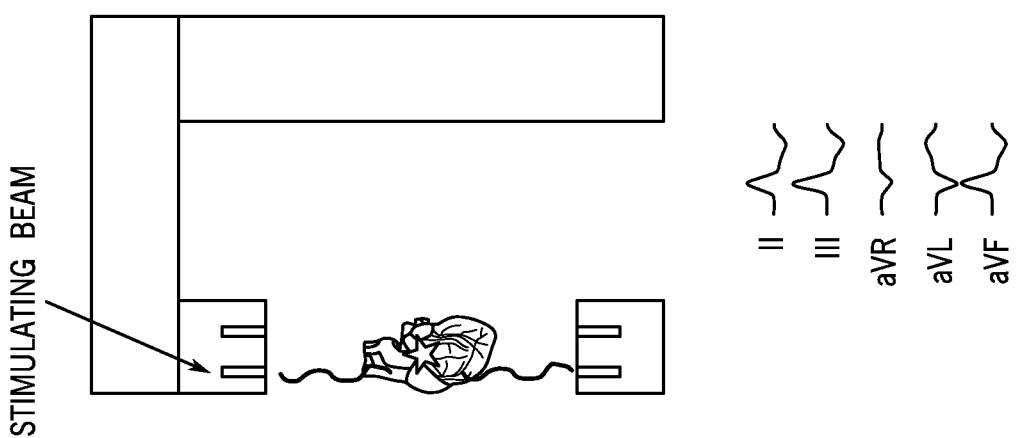
FIG. 14B depicts an example second treatment beam treating tissue, according to one or more embodiments. Acceptance due to "pace map" indicates beams are aligned to same point, and rejection due to difference in "pace map" indicates beams are not aligned. Illustrated are spatially separate beams that may be pulsatile and not necessarily parallel as depicted in this figure. Illustrated are spatially separate beams that may be pulsatile and not necessarily parallel as depicted in this figure. The treatment beam may be effectively used to treat/ablate the arrhythmogenic focus, and repeated stimulation may be applied to help ensure that the required pathological substrate has been successfully ablated.
Figure 15:
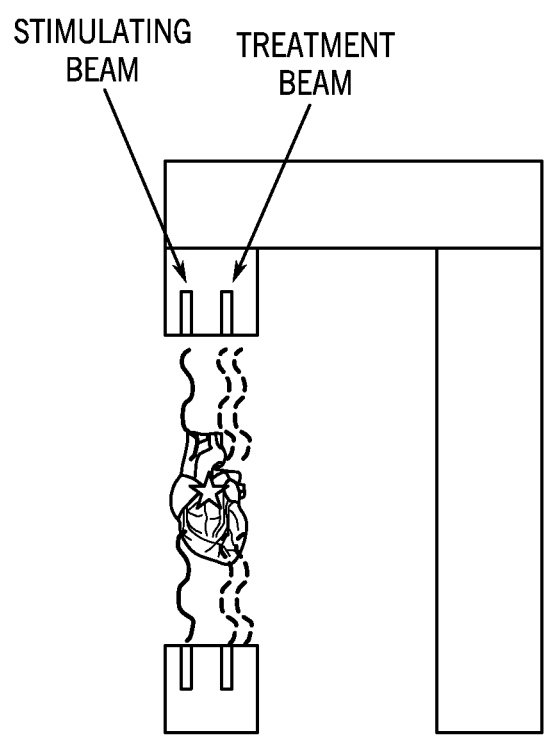
FIG. 15 depicts an example stimulating beam and an example treatment beam, with energy delivered until loss of capture from stimulating beam, according to one or more embodiments.
Figure 16:
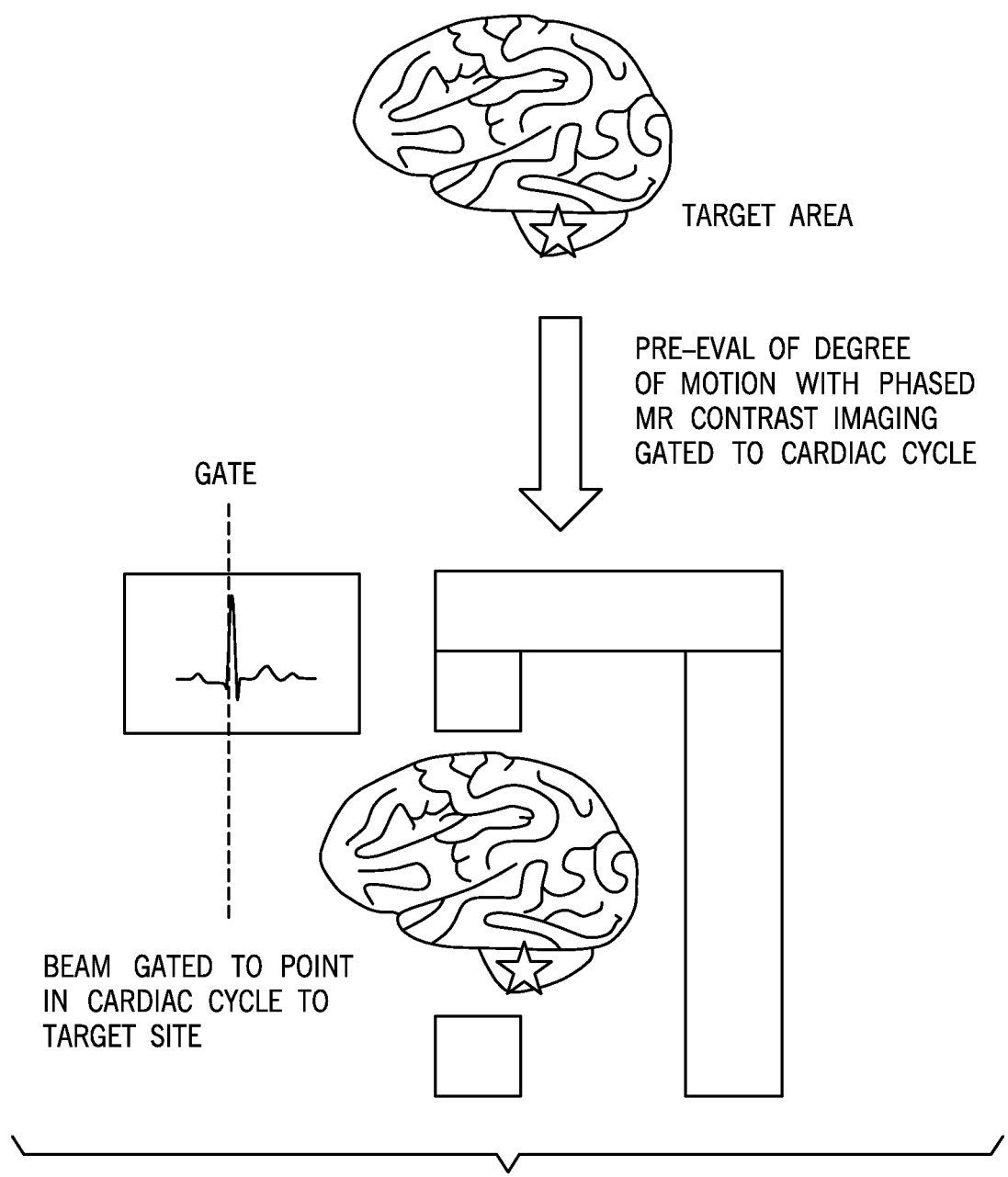
FIG. 16 depicts gating of a beam to the point in the cardiac cycle to target a site of interest, following pre-evaluation of the degree of motion with phased MR contrast imaging gated to cardiac cycle, according to one or more embodiments. Successful energy delivery involves gating and modeling mobile organ movement in three-dimensional space, something that requires a stable identifiable trigger recorded in high digital resolution/frame rate. Illustrated is the use of the electrocardiogram signed off the initiation of the QRS complex. This triggering is particularly important for a complex contractile organ such as the heart but may be used for extracardiac organs including the blood vessels, and perivessel nerves, which may have inherent transmitted pulsation from the neighboring vessels. Electrical triggers may be organ specific such as the use of the electroencephalogram or catheter-based electrocorticogram to trigger, simulate, and guide treatment of epilepsy, depression or compulsive neurosis, and to promote regeneration with low energy delivery to treat disorders such as Parkinson's disease, Alzheimer's disease, Huntington's disease, etc.
Figure 17A:
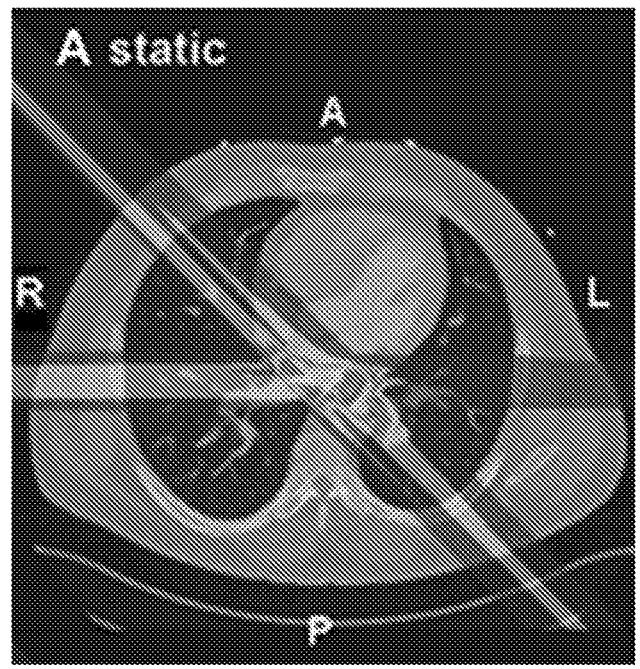
FIG. 17A illustrates tracking of energy delivery location without significant change when cardiac motion occurs when compared to a nonmotile/static modeling. As labeled, R corresponds with right, L corresponds with left, A corresponds with anterior, and P corresponds with posterior.
Figure 17B:
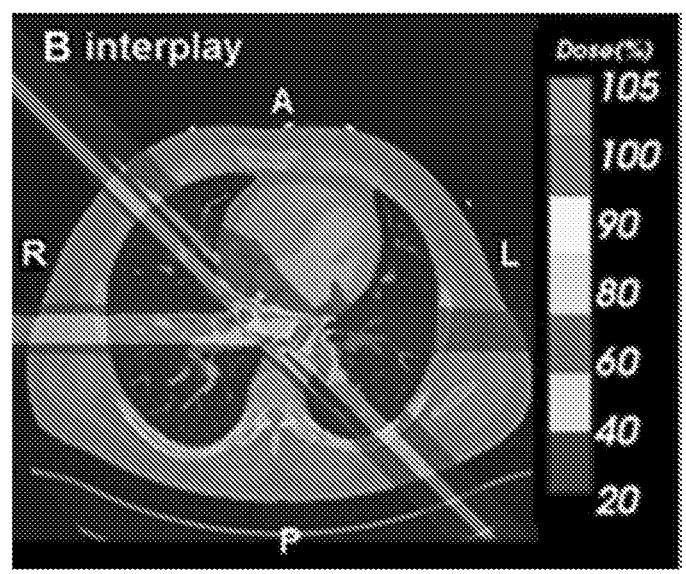
FIG. 17B illustrates tracking of energy delivery location without significant change when cardiac motion occurs when compared to a nonmotile/static modeling. As labeled, R corresponds with right, L corresponds with left, A corresponds with anterior, and P corresponds with posterior.
Figure 17C:
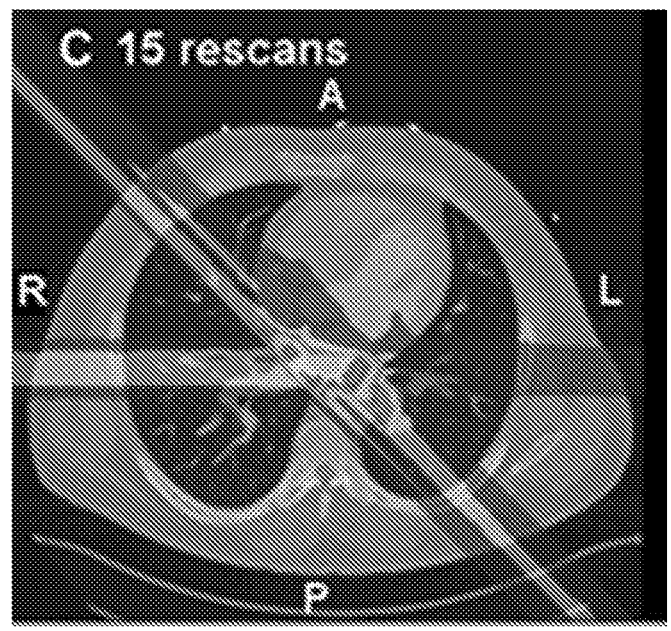
FIG. 17C extends concepts illustrated in FIGS. 17A and 17B when rescanning at a different time point and different portion of the cardiac cycle and illustration in three dimensions.
Figure 17D:
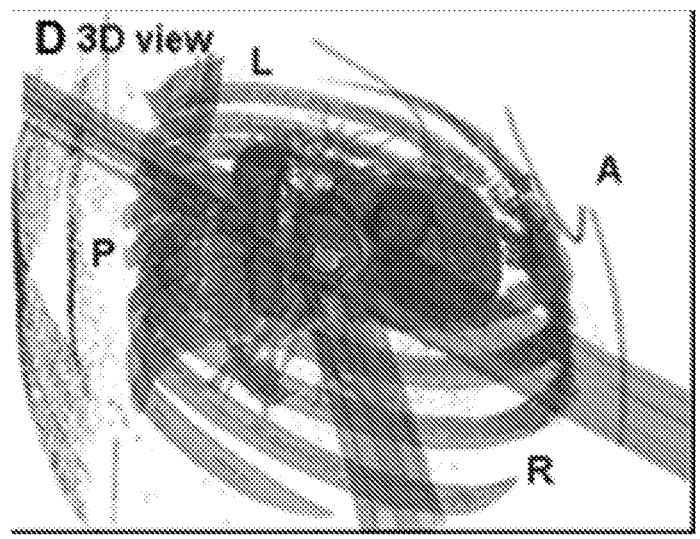
FIG. 17D extends concepts illustrated in FIGS. 17A and 17B when rescanning at a different time point and different portion of the cardiac cycle and illustration in three dimensions.
Figure 18:
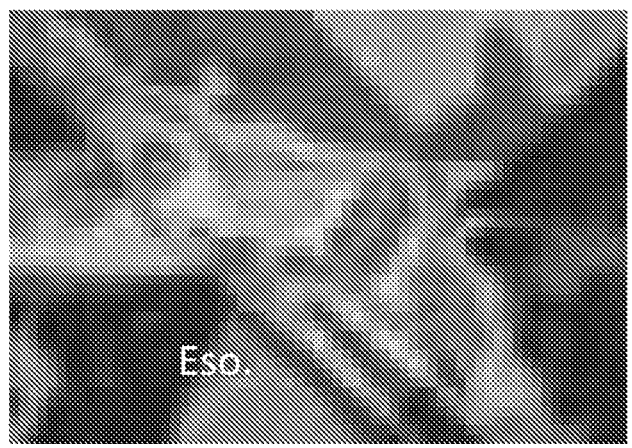
FIG. 18 illustrates targeted delivery of energy without collateral damage to a nonpathological, sensitive structure, in this instance, the esophagus ("Eso").

Manual tissue labeling as well as automated tissue labeling may be used as part of this process (see FIGS. 11A, 11B). Clinicians may manually label tissue based on its appearance, movement (valve versus myocardium), and tissue characteristics (e.g., reflectivity on ultrasound, absorption characteristics on MRI or CT scan, etc.). In various instances, therefore, the first step involves imaging and tissue identification including labeling.

The second step may involves analysis through a cardiac cycle from beat to beat using an index beat as template and correcting for outliers (not fitting the contour or movement from the index beat or beats).

The disclosed approaches enable tagging similar movement of the particle beam delivery tool in a manner superior to simply tagging with an electrical event alone such as the EKG or whole organ movement. This is at least in part due to the fact that whole organs can have complex movement including twisting, translational movement, and transferred movement, along with random movement such as a ruptured chord.

Such TTD contouring can also minimize collateral damage since dramatically different contouring would be seen, for example in the lungs, the ascending aorta, or the esophagus. TTD contouring also helps identify abnormal and arrhythmogenic tissue by assessing differences in contours within a specific chamber myocardium despite similar electrical activation, and conversely, similar contouring with diverse electrical activation pattern as evidenced by EKG vector analysis.

In various embodiments, contouring can provide important feedback information for titration energy delivery. In other words, a contour identified at baseline and deemed arrhythmogenic would change based on differences in registered time and spatial points as a result of successful energy delivery. When such differences exceed preset parameters (such as by 50%), energy delivery may be automatically stopped. Tracking of the contour may be done by any or a combination of observable recorded parameters including the electrocardiographic vector, ultrasound-based distance of a particular structure to the surface of the body, computerized tomograms, impedance changes with an integrated circuitry with a vest of specifically spaced and circumferential electrodes around the organ of interest for energy delivery. These signals are digital, and following appropriate filtering, are fed into the circuitry that allows energy delivery in the accelerator and the accelerator's own focusing mechanism (direction and depth). When, for example, contour change in movement in one direction in three-dimensional space is noted, automatic shifting of the focus and depth of energy beam is accomplished. There may be a learning period with simulated energy delivery over several cardiac cycles prior to actual treatment with a self-learning algorithm when errors in simulated point of energy delivery/focus has been detected when compared to the real time position of the cardiac and other organ contour.

With or without phase contouring, in various embodiments, simultaneous single or multiparticle energy delivery may be used so as to maximize and optimize or otherwise enhance Bragg peak effects of each, and in turn minimize or otherwise reduce unwanted entrance effects and disperse of lesions. These effects along with phase differences may be accentuated with additional administered agents such as contrast microbubbles, calcium chloride infusion, varying infusion rates and salinity of sodium chloride infusion, skin and superficial emollients as well as implanted devices that may be gels or pericardial emollients. Such additions may improve visualization, TTD differences, and create secondary electrical effects that in turn may ablate tissue as a result of activation of the primary particle beam. These agents may also be inhaled so as to better define lung contours to avoid collateral damage when the heart is the target or maximize differences between tumor and normal tissue when lung tissues are the target.

Regarding enhancing Bragg peak effects and reducing unwanted entrance effects, the specificity of the Bragg peak, along with the exactness of the corrected and finalized cardiac contour, allow graded single and multisite energy delivery. Low-dose delivery can be used to induce perturbations in the cardiac contour such as by inducing ectopic (extra) beats. These induced beats' contour will be different with respect to the template obtained over several beats and specific for a region of stimulation. For example, electrocardiographic leads II, III, and aVF will be positive when the test single particle is delivered to the cardiac outflow tracts, etc. A second energy beam or multiparticle energy beam may then be utilized to again test for site of application. The resulting change in contour and electrocardiography will then be matched for templates, and if the area and volumes described differ by less than 5% or similar value, for example, then both beams are considered to be guided to a similar location and additive particulate delivery at low dose so as to further minimize entry effects and collateral damage may be used. Further, one beam may be used to stimulate the tissue while the other to ablate with the inability to stimulate from the first beam being used as an endpoint for energy delivery from the second.

Figure 19:
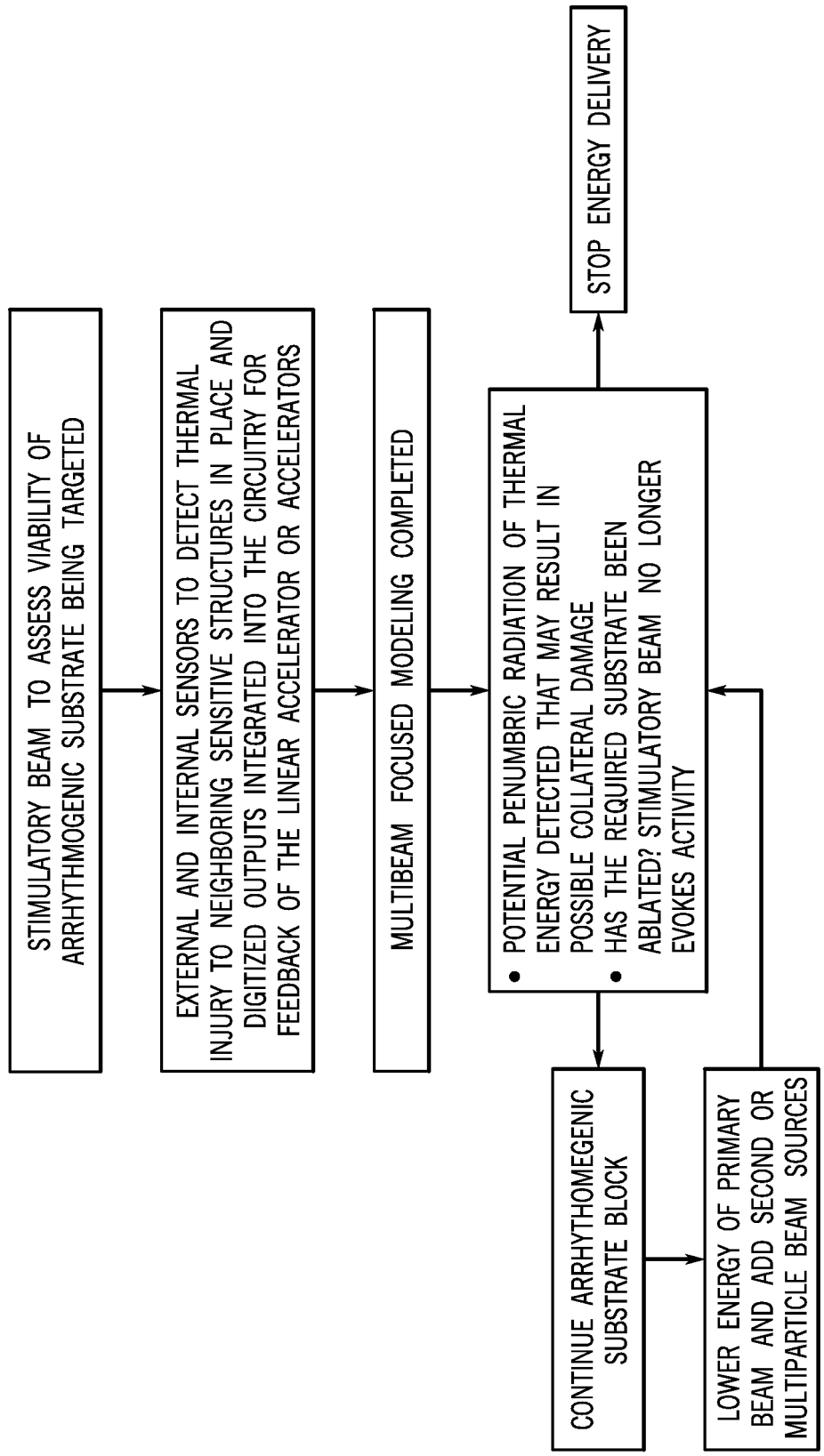
FIG. 19 provides a flowchart depicting an example process for targeted energy delivery in accordance with one or more embodiments of the disclosure.

In some instances, despite the Bragg peak based specificity for site of energy delivery paired with the disclosed tagged contouring described in this document, extreme proximity with sensitive structures may preclude safe energy delivery in certain implementations. In such cases, a stimulating beam is first employed to allow titration of energy delivery and to know an endpoint when the tissue being targeted has been ablated. Similarly, injected or implanted temperature/impedance or thermal map detecting sensors are placed within, at, near, or in a visualizable vantage position for a sensitive structure such as the esophagus or coronary artery. Multiparticle beams are focused on the structure of interest when one beam at a given angle with anticipated depth, etc., creates a penumbra lesion where one of the above mentioned sensors detects potential collateral damage yet based on the stimulatory beam, the site requiring ablation has not yet been completely ameliorated. Then, lower energy with two or more beams focused on that structure is used, and the process repeated at lower and lower energies and more and more multiparticle beam sources until the penumbra volume for thermal injury is minimized and successful ablation has occurred. An example process is depicted in FIG. 19.

Notably, the above test and eventual delivery and contouring may include contouring of thoracic structures during respiratory movement, the esophagus during peristalsis, major blood vessels during systole and diastole, and cross, sagittal, coronal, and long axis imaging (CT, MIBG, MRI, etc.) views through the cardiorespiratory cycles may be continuously validated against each other and composites against an initially established template with any change beyond a manually changeable acceptable error such as 5-10% at noncritical sites, for example, renal autonomics or 0.1-1% near the cardiac epicardial arteries, etc.

To maximize or otherwise enhance efficiency, a new set of tools that include table, armrests, bellows, and intravascular or intra-viscus mirroring reflecting or focusing tools may be used in certain implementations. Existing tools to house patients when being treated surgically or interventionally may not be suitable for certain implementations of the disclosed therapy techniques. Pivot points, angles of movement, and relative position such as if the arms to the head or the body are fixed allowing free movement at varying and programmable positions would not only be ergonomically ideal for static patient therapy delivery modalities but may allow a programmed body phase contouring that negates the effect of a particular tissue's time dependent contouring and thus create a relatively static piece of targeted pathological tissue.

The techniques and approaches discussed above are also applicable to "static" organs. For example, to treat seizures, pulsatility of the brain per se may be minimal, but the abrupt phase change in pulsatility for the brain's blood vessels, particularly the arteries, would be important to define to prevent damage to these structures when treating brain tumors or seizure substrate/foci. Similarly, for renal denervation or other denervation, the artery and vein will serve as localizing phase contours to know where the nerves are located and energy delivery kept to the para phrase of the pulsating contour to avoid intraluminal damage.

It is noted that static organs are not entirely static; for example, internal brain structures pulsate with a different vector loop because of cerebrospinal fluid (CSF) flow rather than the external subdural structures. Phase contouring using either an external electro and cephalogram signal, carotid pulse wave, or cardiac electrogram or combinations of these may be used to create a multi-cycle contour of different brain parts that serve as an electronic trigger to move, in real-time, the beam source to enhance temporal resolution for a given spatial resolution, and enhance the spatial resolution for a given time point.

In other embodiments, a unique diagnostic and stimulatory system based on particle delivery patterns may be implemented. The mechanism for ablation and destruction of pathological substrate inherent in iterations and embodiments described above occurs as a result of the local effects of particle bombardment and transference of energy including to thermal energy. When done in specific pulsed sequences, stimulation rather than destruction would occur serving as a diagnostic tool akin to intravascular electrophysiology study or intracranial epilepsy induction with simultaneous delivery potentially from a bifurcated but focal source of two different particle delivery patterns. Stimulation may continue to occur as destruction is planned with failure to stimulate at a particular output or frequency serving as an endpoint for discontinued tissue viability and thus the absence of need for continued destructive particle therapy.

Specific patterns for specific patients and clinical applications may be required in certain implementations. The input may be from the beating heart or equivalent contour, specific location of the arrhythmogenic substrate, and critical structures that have been imaged and tagged throughout the cycle that need to be avoided for collateral damage.

Further, in various embodiments, particle beam therapy patterns and algorithmic delivery may be used to promote tissue revascularization, iontophoresis-like tissue uptake of chemical agents including drugs, and delivery of biological therapies such as vector-based biological agents. Combined biological and cell therapy delivery tools that may be intra-body along with extra corporal beam therapy are also envisioned to promote and maintain tissue uptake of the biological agent.

Example 1: Atrioventricular Ablation

In one non-limiting example, a study was performed that demonstrates the superior results delivered by the disclosed systems and methods that were not achieved using conventional practices. This study sought to ablate the atrioventricular junction completely noninvasively, using a single-fraction, image-guided application of photon beams in an intact porcine model. The study showed that intensity-modulated radiation therapy can be relatively precisely focused to the atrioventricular junction to noninvasively achieve complete atrioventricular block despite cardiac and respiratory motion. Complete atrioventricular block can be achieved with relatively small x-ray doses, with increasing dose increasing lesion size.

Methods/Study Design: Ten domestic healthy pigs (*Sus scrofa* domestica) of either sex were included at 10 weeks of age and randomized to irradiation of the atrioventricular junction with doses of 25, 40, 50, and 55 Gy.

Anesthesia and Monitoring During Surgical Procedures: Anesthesia was induced using an IM dose of telazol (4.4 mg/kg), ketamine (2.2 mg/kg), and xylazine (2.2 mg/kg). After intubation, animals were ventilated on 1% to 3% isoflurane and monitored using 4 surface ECG electrodes, invasive blood pressure, temperature, and SpO2.

Sedation and Positioning During Computed Tomographic Imaging and Photon Irradiation: During cardiac imaging and photon beam irradiation, animals were sedated using a continuous IV drip of propofol (10 mg/mL; 0.25-0.30 mg·kg$^{-1}$·min$^{-1}$) without additional paralytic use. Animals were immobilized using a vacuum cushion (BodyFIX Blue-BAG; ElektaAB, Stockholm, Sweden) to ensure a stable, reproducible position for computed tomographic (CT) imaging and radiation therapy delivery. The CT reference point (CT laser system) was marked on the skin and on the cushion.

Specific Methods: Specific methods, including electrophysiological study and treatment planning CT acquisition, were conducted using carbon ion ($^{12}$C) beams (as recently described in Lehmann H I et al, Feasibility study on cardiac arrhythmia ablation using high-energy heavy ion beams. Sci Rep. 2016; 6:38895. doi: 10.1038/srep38895.15).

Baseline Study and Electrophysiological Evaluation: The surgical field was shaved and prepped with povidone-iodine solution. A cut-down with subsequent vessel preparation for placement of introducer sheaths in the left/right external jugular vein and right/left femoral arteries and veins was performed. For intracardiac echocardiography, a 10F 5.5 to 10 MHz probe was used (Acuson; Cypress, Mountain View, CA). A 7F decapolar catheter was placed in the coronary sinus. Catheterization was performed under biplane fluoroscopic guidance. Electroanatomical mapping was performed (Carto XP, Biosense Webster, Inc, Diamond Bar, CA). A Navistar or Navistar-Thermocool mapping catheter was used (Biosense Webster). For each chamber, ≈2200 points were sampled, and a fill-threshold <15 mm was considered as adequate to reflect a high-density map. Bipolar signals were recorded between the distal electrode pairs. Signals were displayed and recorded using a digital amplifying and recording system (CardioLab Electrophysiology Recording System, GE Healthcare). Left ventricular function was assessed using left ventricular ventriculography and intracardiac echocardiography. Intracardiac fiducials were implanted at the coronary sinus ostium, right atrial appendage, and left atrial appendage for biplane x-ray and cone beam CT positioning before irradiation (Quick Clip 2; 8×2 mm; Olympus, Shinjuku, Japan).

Pacemaker Implantation: All animals underwent pacemaker implantation at the end of the baseline electrophysiological evaluation. After removal of the sheath from the external jugular vein, two 7F active fixation pacing leads were introduced through 2 small incisions in the vessel wall. Atrial leads were placed in the right atrial appendage, and right ventricular leads were placed in the right ventricular apex. Leads were tunneled and connected to a pacemaker unit placed in a subcutaneous postauricular pocket (Medtronic, Inc, Minneapolis, MN).

Treatment Planning CT Acquisition: Cardiac-gated native and contrast-enhanced CT scans were acquired for photon beam treatment planning on a 64 row Siemens Somatom Definition Flash scanner (Siemens Healthcare, Forchheim, Germany). Contrast-enhanced scans were obtained after injection of 50 mL contrast agent (4 mL/s; 8-10 seconds delay; Omnipaque 350 mg I/mL; GE Healthcare) through a cannula in a branch of the caudal auricular vein. All scans were acquired at expiration using a pause of the respirator. Ten cardiac phases with 1 mm voxel and slice spacing were reconstructed with an enhanced field of view of 400 mm for skin-to-skin images to be used for radiotherapy planning.

Contouring and IMRT Treatment Planning: A sphere of 5 mm diameter was contoured as atrioventricular junction ablation lesion on all 10 cardiac phases. The average contour position was subsequently transferred into the phase-averaged CT scan that was used for all subsequent treatment planning steps. Organs at risk for beam delivery were contoured on the averaged CT as well. All treatment planning was conducted using Eclipse (Varian Medical, Palo Alto, CA) treatment planning software. Cardiac motion was incorporated by anisotropic expansion of the target (±1 mm left-right, ±4 mm superior-inferior, and ±4 mm anterior-posterior). In addition, a margin of ±4 mm was added for positional uncertainty and residual respiratory motion. All treatment plans were computed using 2 or 3 arcs. Dose restrictions from single-fraction x-ray deliveries were used for treatment plan computation; restrictions to coronary arteries were included into the dose optimization process.

Animal Repositioning and Photon Irradiation of the Atrioventricular Junction: At the time of treatment, animals were initially aligned in the BodyFIX bag using an in-room laser system and skin markings. Subsequently, isocenter position was refined using matching of bony anatomy in 2 digitally reconstructed radiographs derived from the CT scan compared with 2 orthogonal in-room x-ray images. The match was finalized using position of the CS ostium fiducial clip on in-room (cone beam) CT, conducted during expiration and inherently averaged during the cardiac cycle. Beam delivery of 6 MV photons was gated to expiration and was performed using a linear accelerator (True Beam; Varian Medical).

Follow-Up After Irradiation: Animals were followed for weeks after irradiation. Device interrogations were performed after 4, 8, and 12 weeks and at termination of follow-up where the animals also underwent a procedure identical to the one conducted at baseline as described above. Animals were euthanized through induction of ventricular fibrillation directly followed by exsanguination.

Pathological Examination: Heart, lungs, trachea, phrenic nerves, and esophagus were removed en bloc with the pericardium intact. Triphenyltetrazolium chloride (Sigma Aldrich, St Louis, MO) was used to delineate the ablation lesions. Gross pathological findings were assessed, and all macroscopically visible lesion dimensions were measured on the endocardial surface in the nonfixed tissue. Lesion volumes were calculated as described in infarcted tissue.

Histological Examination: For histological analysis, samples were fixed in 10% formaldehyde and processed. After fixation, samples were wax embedded and cut with a microtome. Cut sections (5 μm) were stained with hematoxylin and eosin and Masson trichrome staining and evaluated using light microscopy.

Statistical Analysis: All statistical analyses were performed using SPSS 18. Baseline characteristics in Table 1 are depicted as mean±SD. Treatment planning data in Table 2 is depicted per individual case. Spearman correlation was used for bivariate correlations between the administered dose, the lesion area in electroanatomical mapping, and the calculated lesion volume. Isodose lines were correlated with electroanatomical lesion findings and macro and microscopic lesion outcomes. Median time to complete atrioventricular block was estimated using the Kaplan-Meier estimation model, treating the animal that died prematurely as censored observation. A P value <0.05 was used as cutoff value to indicate statistical significance.

TABLE 1

Table 1: Baseline and Follow-Up Characteristics of All 10 Animals Included Into the Analysis

|  | All Pigs (n-10) | Sham Control (n = 3) | AVJ 25 Gy (n = 2) | AVJ 40 Gy (n = 2) | AVJ 50 Gy (n = 1) | AVJ 55 Gy (n = 2) |
|---|---|---|---|---|---|---|
| Mean weight at imaging, kg | 32.02 ± 3.6 | 32.5 ± 4.6 | 31 ± 3 | 34 ± 2 | 28 | 30.4 ± 0.4 |
| Mean weight at irradiation, kg | 32.5 ± 3.8 | — | 32 ± 4 | 33 ± 2 | 29 | 31.4 ± 0.4 |
| Mean duration of follow-up, d | 124.8 ± 30.8 | 18.7 ± 5.6 | 111 | 125 ± 0 | 82 | 138 ± 13 |
| Mean time from CT to irradiation, d | 4.3 ± 1.6 | — | 6 ± 1 | 5 ± 0 | 3 | 2.5 ± 0.5 |
| Target contour diameter (CTV), cm | 0.5 | — | 0.5 | 0.5 | 0.5 | 0.5 |
| Volume receiving target dose, mL | 2.5 ± 0.5 | — | 2.8 ± 0.2 | 2.0 ± 0.4 | 1.9 | 2.8 ± 0.1 |
| Setup time (first image to beam), min | 33.0 ± 11.7 | — | 36.0 ± 15.8 | 24.3 ± 0.9 | 49.4 | 30.6 ± 1.8 |
| Irradiation time (beam on to beam off) | 17.2 ± 6.3 | — | 9.9 ± 0.5 | 14.7 ± 2.0 | 19.9 | 25.7 ± 0.3 |
| Total procedure time | 50.2 ± 13.5 | — | 45.9 ± 16.2 | 39.0 ± 2.9 | 69.3 | 56.3 ± 2.1 |

TABLE 2

Table 2: Resulting Mean Doses to Organs at Risk From Treatment Planning for Atrioventricular Junction Ablation: Doses are stated for all organs at risk. Only the coronary arteries had to be included into the beam and dose optimization process. Included are only treated, but not sham-animals. In the 50 Gy case, a less strict threshold was applied for protection of the coronary arteries from dose. LCA indicates contour encasing the left anterior descending and the circumflex coronary arteries; and RCA, right coronary artery.

| Case No. | Dose, Gy | Maximum Dose in Target | LCA, Gy | RCA, Gy | Trachea, Gy | Skin, Gy | Esophagus, Gy |
|---|---|---|---|---|---|---|---|
| 1 | 55 | 60.7 | 6.8 | 6.0 | 14.1 | 13.4 | 12.6 |
| 2 | 55 | 60.4 | 7.1 | 6.5 | 15.3 | 12.7 | 11.4 |
| 3 | 50 | 53.5 | 9.5 | 9.0 | 9.2 | 9.7 | 7.7 |
| 4 | 40 | 45.7 | 4.7 | 4.3 | 11.1 | 10.3 | 9.6 |
| 5 | 40 | 44.8 | 4.6 | 4.0 | 13.0 | 8.3 | 9.8 |
| 6 | 25 | 28.9 | 2.7 | 2.3 | 7.0 | 4.8 | 5.2 |
| 7 | 25 | 29.2 | 2.7 | 2.3 | 7.9 | 5.8 | 6.3 |

Results/General Characteristics: Out of 10 animals, 2 animals were treated with a prescription dose of 55 Gy, 1 animal received 50 Gy, 2 animals received 40 Gy, and 2 animals were treated with 25 Gy. General characteristics of all animals are shown in Table 1. The mean animal weight at baseline was 31.7±2.7 kg. The mean follow-up duration was 120.7±7 days. The mean weight gain during the course of the follow-up was 61.1±5.2 kg. The mean left ventricular ejection fraction at baseline was 70±5%.

Figure 2:
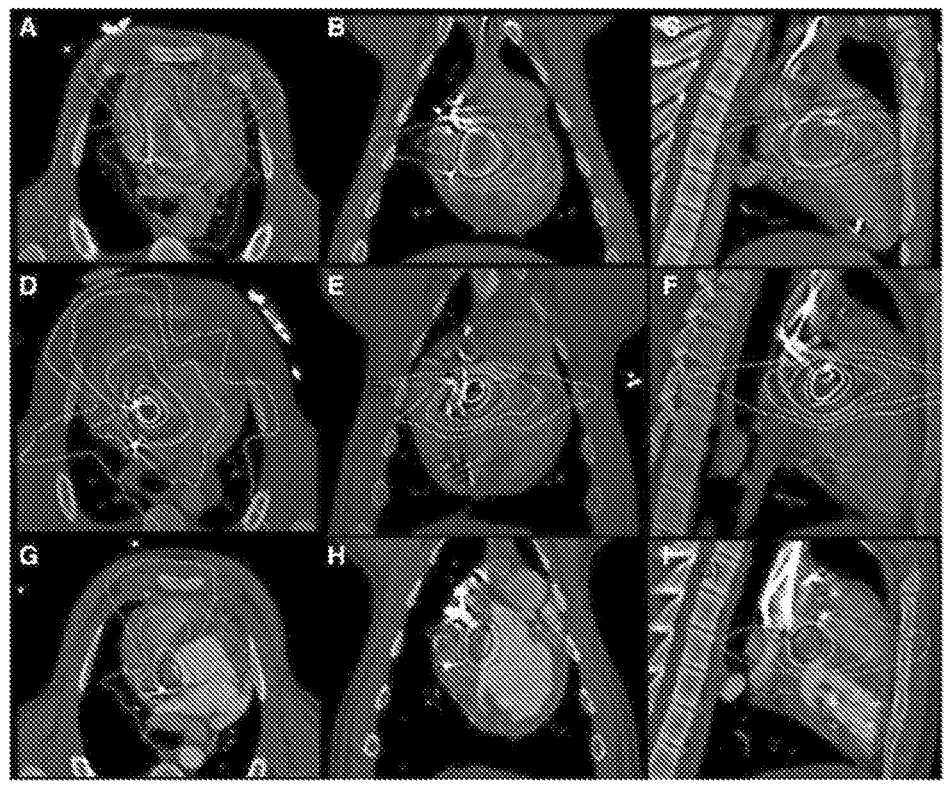
FIG. 2 shows treatment-planning outcomes for 3 different doses for irradiation of the atrioventricular junction, in accordance with one or more non-limiting example embodiments. Note that the lower dose does not conform to the target volume because the dose restrictions to the coronary arteries were given high priority in the optimizer. This choice led to relatively high doses in the interventricular septum. A, Axial view, (B) sagittal view, and (C) coronal view for the 55 Gy administration. Following images depict 40 and 25 Gy with views in the same order. LA indicates left atrium; LAA, left atrial appendage; LL, left lung; LV, left ventricle; RA, right atrium; RL, right lung; RSPV, right superior pulmonary vein; and RV, right ventricle.
Figure 2:
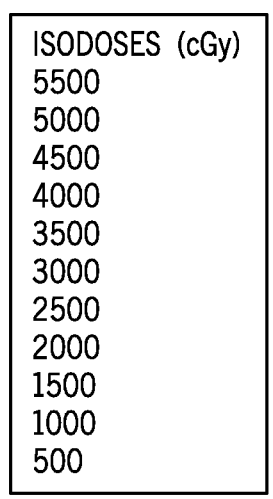

Contouring and Treatment-Planning Outcomes: FIG. 1 depicts contouring outcomes used for subsequent treatment plan computation, including the target as well as cardiac and surrounding risk structures. The atrioventricular junction ablation lesion was contoured in the superior portion of the triangle of Koch. The mean volume receiving the prescription dose for atrioventricular junction ablation was 2.5±0.5 mL (including blood; Table 1) after target motion and tissue deformation was included. The maximal point doses per individual case to the coronary arteries, esophagus, trachea, and skin are depicted in Table 2. FIG. 2 shows 3 actual treatment-planning outcomes for delivery of 55, 40, and 25 Gy to the atrioventricular junction in 3 planes. Restriction of the maximal allowed point dose to the coronary arteries led to a dose distribution that did not have perfect conformity with the target volume, producing relatively high doses anterior to the target volume.

Photon Beam Delivery: The mean irradiation time for all groups was 14.3±2.8 minutes (Table 1). Beam delivery for all animals was gated to the expiration phase of the respiratory cycle with a mean duty cycle of 60%.

Figure 3:
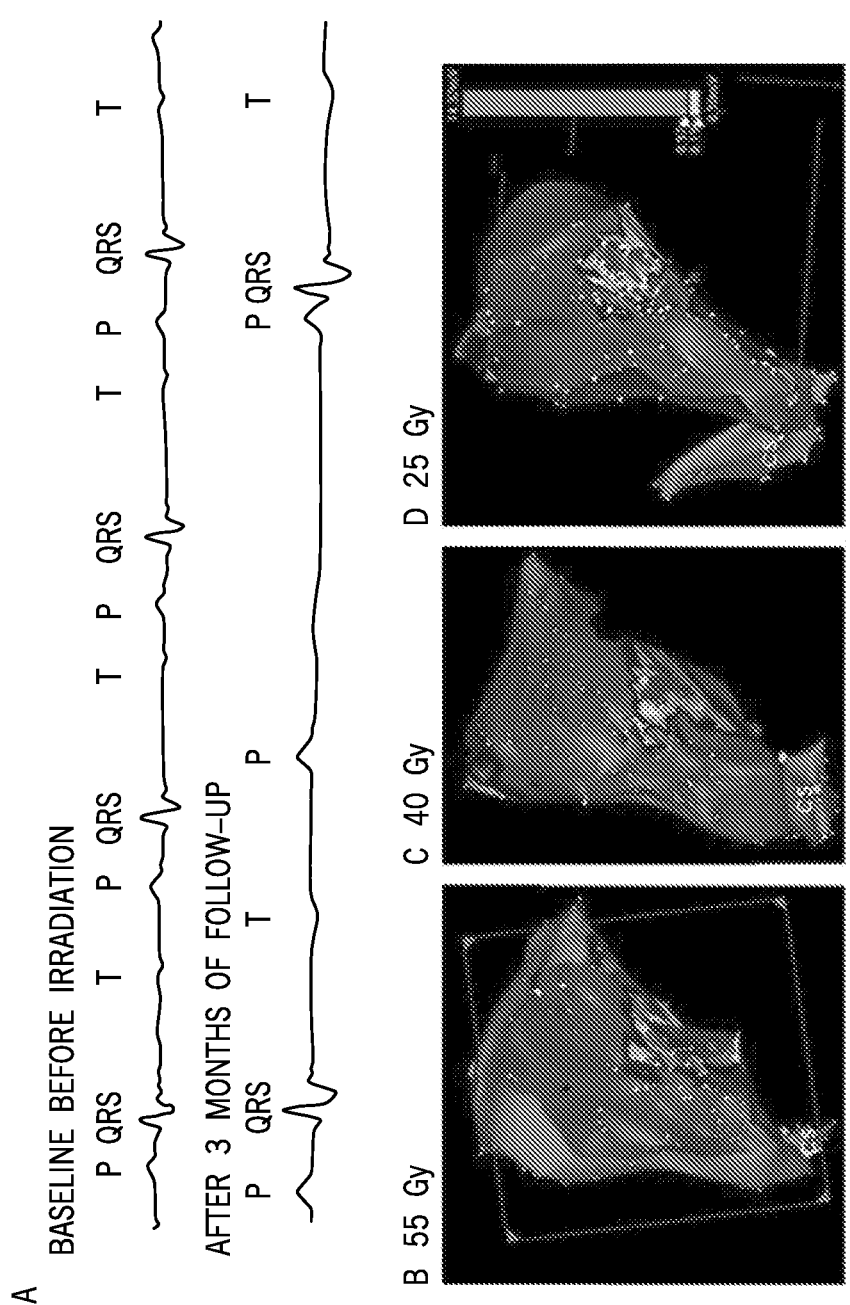
FIG. 3 shows, in accordance with one or more non-limiting example embodiments: A, Top, Surface ECG at baseline before irradiation, showing sinus rhythm. Bottom, Three months after irradiation with 50 Gy, development of complete atrioventricular block with dissociation of atrial and ventricular activity. B, Right lateral view of the septal site of endocardial voltage maps 3 months after irradiation with 55, 50, 40, and 25 Gy for electroanatomical lesion characterization. All animals had complete atrioventricular block present at the time of mapping. The coronary sinus is marked. Voltage thresholds as depicted on the color bar on the right-hand side.
Figure 4:
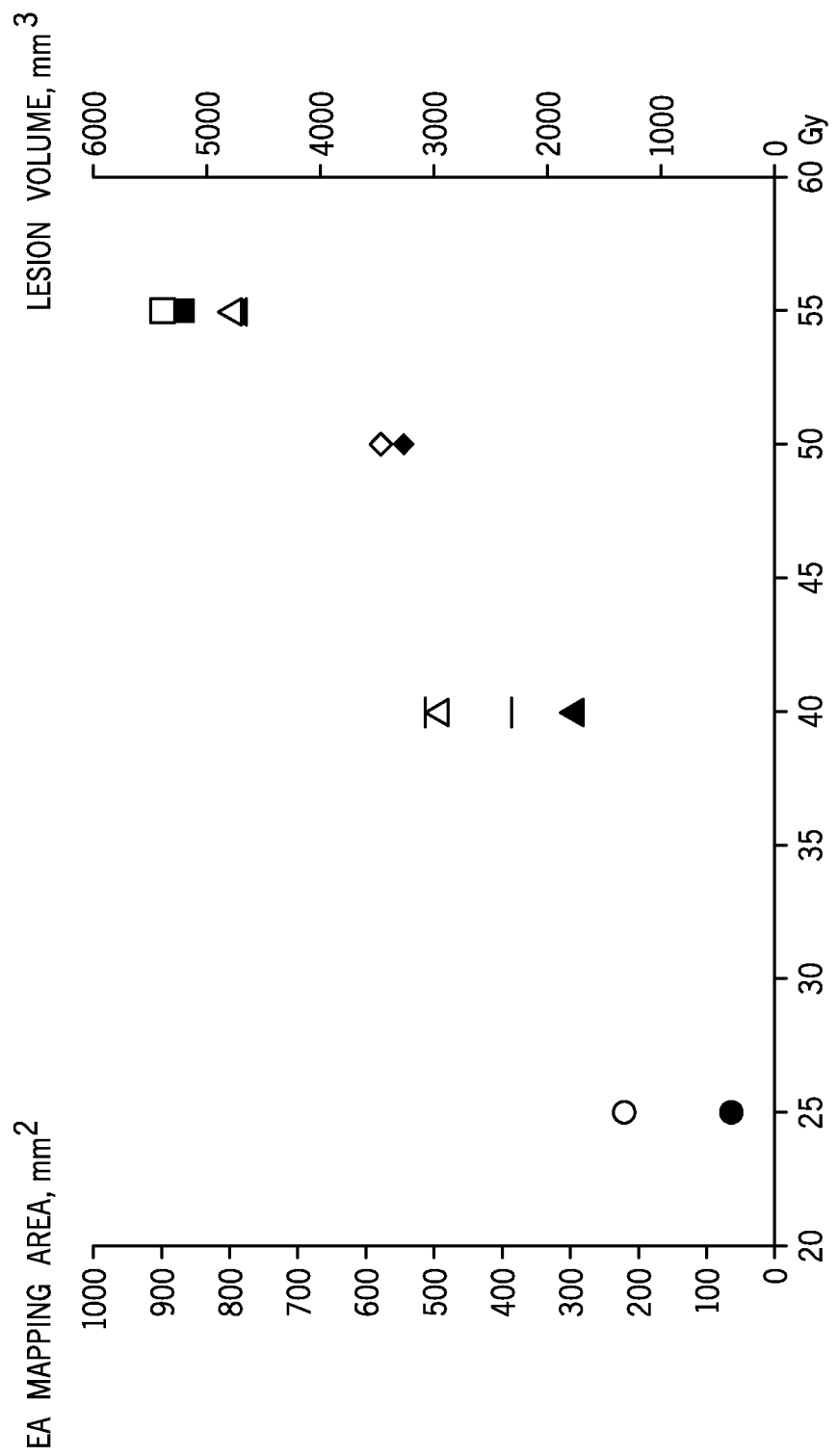
FIG. 4 shows, in accordance with one or more non-limiting example embodiments, lesion area from electroanatomical mapping in the right atrium (red markers), plotted along with the calculated macroscopic lesion volume after necropsy (blue markers) against the dose administered to the target volume-One marker symbol represents data for one animal, respectively. Ordinate and abscissa are as labeled.

Electrophysiology and Outcomes After Irradiation: The median time until complete atrioventricular block occurrence was 11.2 weeks (SE: 0.490) post-irradiation and developed in 6 out of 7 animals (86%; 1 animal [25 Gy] died prematurely of device-related infection and could not be evaluated in a similar fashion). For in vivo characterization of the lesion size that led to atrioventricular block, electroanatomical mapping was conducted. Results of electroanatomical mapping are shown in FIG. 3. The size of the endocardial surface area without electrogram positively correlated to the administered dose (rs=0.971; P=0.001; FIGS. 3 and 4). Complete atrioventricular block was persistent in all animals; in case of the animal treated with 25 Gy, block occurred during the follow-up study of this animal during mapping of the atrioventricular junction.

Figure 5:
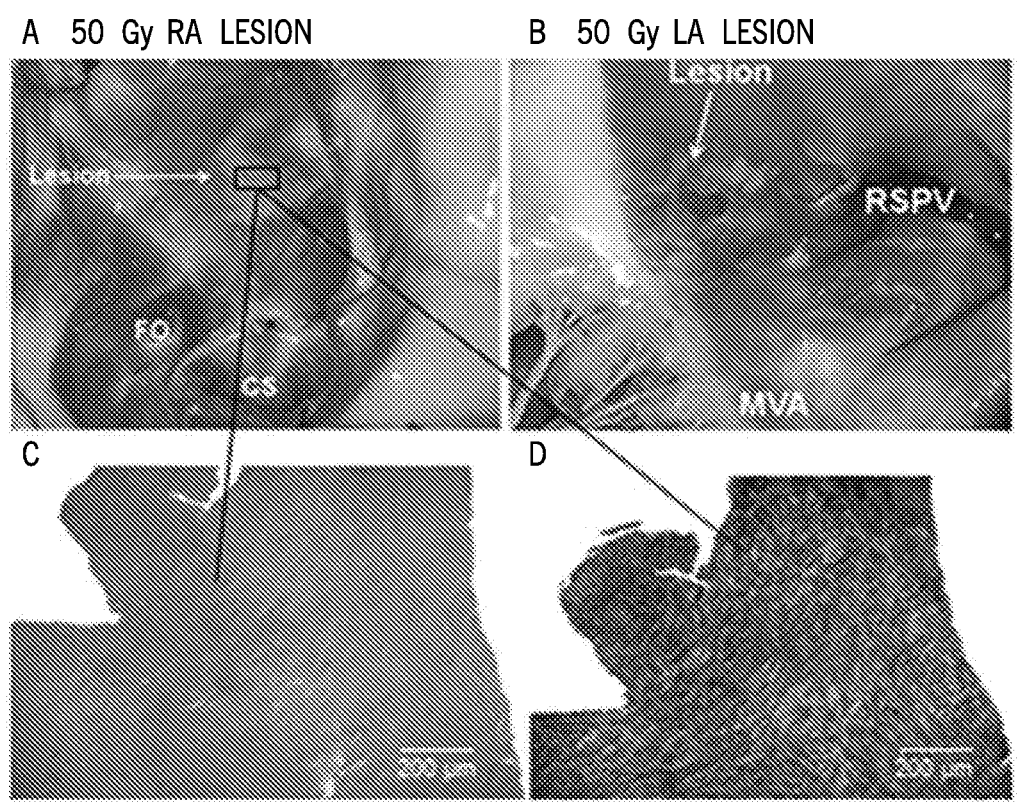
FIG. 5 shows, in accordance with one or more non-limiting example embodiments, representative lesion area for atrioventricular junction (AVJ) ablation in the right (A) and left atrium (B) after irradiation with 50 Gy. The right atrium is opened through the vena cava, and the left atrium is opened over the mitral annulus. Lesions are marked with arrows. Histological cross-sections of the ablation lesion in the triangle of Koch shown in (C) hematoxylin and eosin and (D) Masson trichrome. CS indicates coronary sinus ostium; FO, fossa ovalis; MVA, mitral valve annulus; and RSPV, right superior pulmonary vein. (*Radio-opaque marker.)

Macroscopic Lesion Outcomes and Correlation to Dose: The positive correlation of macroscopic lesion outcomes with the mapped area and the administered target dose is shown in FIG. 4. Bivariate analysis revealed a positive correlation of rs=0.971; P=0.001, for the calculated macroscopic lesion volume and administered dose. An exemplary macroscopic lesion, consisting of macroscopic visible fibrosis in the right atrial target region is shown in FIG. 5A. In addition, isodose line extension led to lesion development in the septal left atrium (FIG. 5B). The mean right atrial lesion volume on pathological analysis for all dose groups was 3.8±1.1 mL. The mean right atrial lesion volume in the 55 Gy group was 5.1±2.9 mL. The mean right atrial lesion volume in 40 Gy was 3.0±1.0 mL and in 25 Gy was 2.6 mL. In case of 55 and 40 Gy animals, concordantly to the treatment-planning outcomes, lesions extended anteriorly into the right ventricle and interventricular septum. The mean maximal width of lesion extension into right ventricular myocardium was 17.2±9.1 mm.

Lesion Histology/Target Histology: Target tissue analyzed after 3 months of follow-up revealed dense fibrosis, present in the target tissue in all animals of all dose groups (FIGS. 5C and 5D). Similarly and consistent with macroscopic pathology, fibrosis extended anteriorly to the contoured area into the interventricular septum in all 3 dose groups.

Short-Term Toxicity: No collateral damage was observed in the esophagus, trachea, or other organs at risk. The myocardium of the coronary sinus was also spared in all cases. Coronary arteries did not show a reaction within 3 months of follow-up. No radiation-induced side effects were observed during 4 months of follow-up. The left ventricular ejection fraction did not change during follow-up between sham and irradiated animals (Table 2).

Discussion/Main Findings: In this study, we ablated the atrioventricular junction catheter-free using a 6 MV photon beam. Doses of 25 to 55 Gy created lesions that subsequently led to complete atrioventricular conduction block. Point doses to the coronary arteries were optimized to stay <10 Gy, and accordingly, ablation lesions were not fully target conformal. Lesion volumes positively correlated with isodose line spread around the target volume and increased with the administered target dose, despite the use of the same targeting margins in each dose group. Targeted tissue revealed dense fibrosis. Fibrosis was not present in myocardium of beam entry channels, however, histology revealed evidence of cardiomyocyte apoptosis in these areas.

External Photon Beam Radiation for Catheter-Free Ablation: In these presented chronic intact animal studies, photon beams could be appropriately focused for atrioventricular node ablation. Similar to our data with carbon ions ($^{12}C$), reliable ablation was achieved with 40 Gy. This study illustrates the biophysics of photon beams; the ultimate lesion size will depend on the irradiated target volumes, that is, the target dose and optimization constraints that will shape the dose distribution. Previous studies using the CyberKnife photon accelerator indicated that a dose as low as 25 Gy of photons may create an electrophysiological effect. Our here-presented data support this finding for the here-irradiated volume, in which 25 Gy caused a lesion. The time frame for development of atrioventricular block in this study was similar to the CyberKnife studies and faster than what we have observed with $^{12}C$ beams.

Irradiation of a Moving Target With External Photon Beams: Even though photon beams are robust in the presence of target motion, to guarantee dose delivery in the presence of contractile target motion, the approach used in this study was to expand the target volume to cover the whole amplitude of contractile motion, a method used for the treatment of mobile tumors in radiation oncology. This conservative approach was chosen to ensure full coverage of the target with the prescription dose, thus allowing investigation of the required dose to achieve the desired ablation effect in the respective target volume. Other techniques, discussed below in the context of other implementations, allow for, for example, gating of the photon beam to the ECG to decrease the required irradiation margin size. Respiratory motion could already be well mitigated with an acceptable efficiency by using gating of the beam to the expiration phase of the respiratory cycle.

Photon Beams Versus Particle Beam Sources: This study illustrates how sparing of risk structures (e.g., coronary arteries) is possible using photon beams, but how this also leads to higher doses at another location, explaining the observed anterior lesion extension into the interventricular septum. In this study, the volume irradiated with high and low doses of photons is larger than that in our study using $^{12}C$ particle beams. This translated into not only a greater lesion size but also greater involvement of myocardium located in the beam entry channels. This is because of the different physical properties of these 2 energy sources and the chosen beam arrangements. In photon beam radiation therapy, multiple beam angles are used to concentrate dose in the target region where the beams overlap and distribute the entry and exit dose of beam, leading to a larger myocardial volume receiving low-dose radiation. For the plans in this study, each arc comprised 178 distinct photon beams. Longer-term follow-up times after irradiation will reveal long-term effects for lesions creation and of exposure of these larger myocardial volumes in comparison to the different forms of particle therapies ($H^+$, $^{12}C$, $^{4+}He$).

Clinical Implications: Adjusting for the differences in anatomy and position of risk structures in the porcine heart as compared to humans, and adjusting doses, which are dependent on the finally irradiated myocardial volume and the irradiated myocardial location, the implementation used in this study is applicable to, for example, cardiac arrhythmia ablation in humans. Arrhythmia ablation without the use of catheters has pertinent clinical implications. After we performed these initial atrioventricular node ablation studies, we have successfully conducted deliveries for pulmonary vein isolation and ventricular myocardial irradiation in the nonarrhythmic animal model. Success rate of catheter ablation in both diseases is still limited, driving our investigations with photon and particle beam therapies. The physical properties of photon beams could make these beams an attractive energy source for ablation whenever larger, deeply situated myocardial volumes are treated that do not require extremely sharp energy fall-off and that can neither be reached from the endo- or epicardial surfaces.

This is the first systematic study using several doses of external photon beam therapy for atrioventricular node ablation in intact animals. Using this respective target volume, doses as low as 25 Gy caused electrophysiological and structural myocardial ablation effects. Doses ≥40 Gy created reliable ablation with interruption of cardiac impulse propagation. As discussed above, this study illustrates certain implementations in certain embodiments and does not limit other implementations of these and other embodiments.

Example 2: Treatment of Cardiac Arrhythmias

In another non-limiting example, another study was performed that demonstrates the extension of 4D treatment dose reconstructions to cardiac motion for ion beam ablation of cardiac arrhythmias in an animal model.

Materials and Methods/Animal cohort: The animal numbering is identical in both publications. An overview of the animal cohort is given in Table 3 (Animal cohort with target (AV: atrioventricular node, LV: left ventricle, PV: pulmonary vein isolation) and dose groups used for the ion-beam ablation study at GSI. The pigs included in the dose reconstruction analysis are marked bold-faced.) Animals received carbon ion beam treatment to three different target areas: (1) the atrioventricular junction (AV), (2) the left ventricular free wall (LV), and (3) the junction of the left atrium and the pulmonary veins (PV). For the AV, different target doses were used to study dose-effect relations. For the purpose of this study, the targets differ mainly in size and position, leading to different nearby OARs and to slightly different motion.

TABLE 3

Table 3: Animal cohort with target (AV: atrioventricular node, LV: left ventricle, PV: pulmonary vein isolation) and dose groups used for the ion-beam ablation study at GSI. The pigs included in the dose reconstruction analysis are marked bold-faced.

| animal | target | dose [Gy] | TV [cm³] | PTV [cm³] |
|---|---|---|---|---|
| 1 | AV | 55 | 0.1 | 1.8 |
| 2 | AV | 55 | 0.1 | 1.7 |
| 3 | AV | 55 | 0.1 | 1.7 |
| 4 | AV | 40 | 0.1 | 1.7 |
| 5 | AV | 40 | 0.1 | 1.8 |
| 6 | AV | 40 | 0.1 | 1.8 |
| 7 | AV | 25 | 0.1 | 1.7 |
| 8 | AV | 25 | 0.1 | 1.7 |
| 12 | PV | 40 | 1.3 | 16.1 |
| 13 | PV | 40 | 0.9 | 11.1 |
| 14 | PV | 30 | 1.0 | 12.6 |
| 15 | LV | 40 | 2.1 | |
| 16 | LV | 40 | 2.3 | |
| 17 | LV | 40 | 2.4 | |

Treatment planning and delivery: Briefly, both imaging and irradiation were performed using a custom-built immobilization device and enforced breath-holds of up to 60 sec to suppress respiratory motion. CT data for treatment planning was acquired for all animals using a Siemens Biograph mCT (Siemens Healthcare, Erlangen, Germany). For each animal, a surface ECG triggered, contrast-enhanced (CE) and non-contrast enhanced 4D-CT was acquired. While internal cardiac motion was visible only on the CE 4D-CT, the native CT was used to calculate ion stopping power. For each scan, 10 equally distributed 4D-CT phases of the cardiac cycle were reconstructed and used as a basis for treatment planning.

Cardiac motion was assessed using deformable image registration (DIR) of the CE 4D-CT with Plastimatch (Shackleford et al., 2010) to obtain the deformation vector fields (see Table 3 for details). The vector fields were used in conjunction with the native CT to compute 4D-doses using correct estimates for both motion and beam ranges. Targets and OARs were delineated and propagated to all 4D-CT phases. Margins were added to the targets, and subsequently a range-considering ITV (see Graeff C et al., 2012, Motion mitigation in intensity modulated particle therapy by internal target volumes covering range changes Med. Phys 39 6004-13) was computed to form the planning target volume (PTV). For all targets, two laterally opposing fields were used. Plan optimization was performed on the resulting planning target volume (PTV) and the native 4D-CT 0% phase, but dose evaluation used 4D-dose calculation under several simulated motion scenarios.

Treatments were delivered at the fixed horizontal beam line of GSI, Darmstadt. The beam was gated except during enforced breath hold of up to 60 sec. During these breath holds, irradiation was carried out over the whole cardiac cycle. All plans were rescanned to mitigate interplay following an inhomogeneous slice-by-slice scheme with 15 rescans in the slice of highest energy and 1 rescan in the lowest. The rationale for this scheme was a reduction in the irradiation duration of around 60% while still achieving adequate 4D-target coverage in treatment planning.

Figure 6:
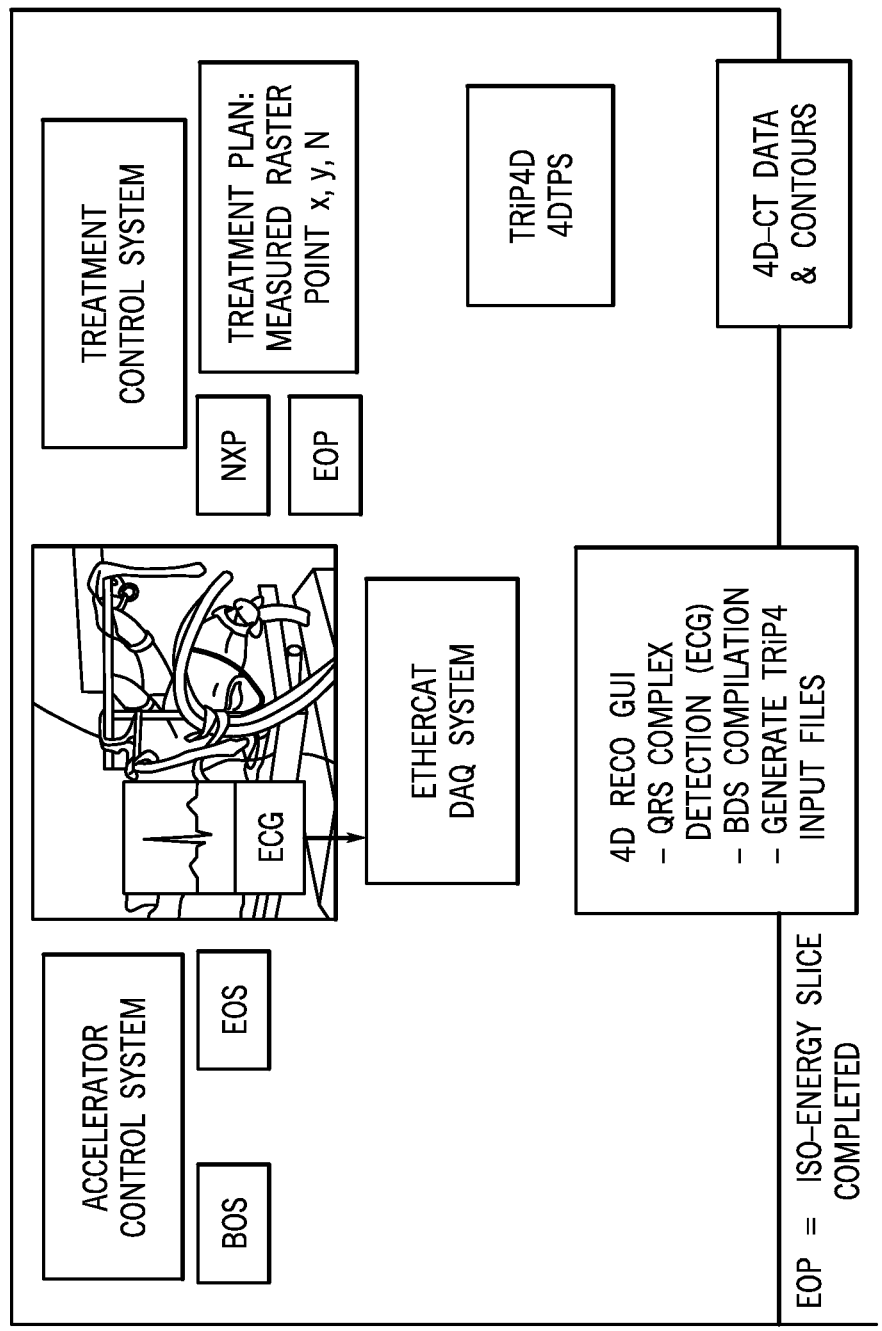
FIG. 6 shows data acquisition and 4D reconstruction workflow, in accordance with one or more non-limiting example embodiments. ECG signal and beam delivery events BOS, EOS, NXP and EOP are acquired in real-time with the data acquisition system (EtherCAT DAQ). The measured position x,y and particle number N of each raster point is then processed according to the NXP sequence using a custom developed GUI to produce input and command files for 4D-dose calculation with TRiP4D.

ECG signal and beam delivery sequence events: A scheme of the data acquisition system and the acquired signals is given in FIG. 6. We implemented a real-time data acquisition system (DAQ) to simultaneously acquire the surface ECG signal of the animals and the synchronized beam delivery sequence (BDS) using a set of signals provided by the control system. The BDS constitutes the temporal structure of the beam delivery, i.e. the time points at which the beam is switched on or off or at which the irradiation of individual raster points is completed (see FIG. 7). Data acquisition of all signals was performed at a sampling rate of 1 kHz using a Beckhoff EtherCAT system (Beckhoff Automation, Verl, Germany).

Delivered treatment plans: The GSI TCS provides acquisition of the actually delivered beam parameters applied per pencil beam. In detail, these are: (i) The actual lateral pencil beam positions in two dimensions (x,y) as controlled by the position feedback of the beam monitoring system; and (ii) The actually delivered particle number (N) as measured with the ionization chambers of the beam monitoring system, including daily calibration factors. We have incorporated these measured data from the GSI treatment records into actual delivered treatment plans entering into our 4D calculations instead of the nominal treatment plans (see also FIG. 6). Due to incomplete treatment records after recovery from an interlock during delivery, 4D-dose reconstructions could not be performed for 3 out of 14 irradiated animals (see Table 3).

4D-dose reconstruction interface: A custom developed graphical user interface (GUI) has been implemented using Python and the PyQt framework to provide an intuitive platform to guide the user through the 4D-dose reconstruction stages (see FIG. 1). The GUI served as a database to manage the acquired ECG and BDS data as well as animal-specific treatment planning data. Further signal processing steps were performed triggering external programs and keeping track of the results. Moreover, the GUI was used to generate and organize the required input and steering files for 4D-dose calculation with TRiP4D. Resulting 4D-dose distributions were fed back into the GUI's database and could be communicated to external visualization software for further analysis. In the following sections, the ECG signal processing and 4D-dose calculation steps are described in detail.

R-wave detection algorithm: The ECG signal recorded during irradiation was used as a motion surrogate to map phases of the ECG cycle to the corresponding 4D-CT phase. To this end, the R-waves of the surface ECG (see FIG. 1) were detected with a non-real-time signal processing algorithm based on the method described by Pan and Tompkins (See Pan J and Tompkins W J 1985 A real-time QRS detection algorithm IEEE Trans Biomed Eng 32 230-6). The algorithm was implemented in an in-house C program as follows:

1. Pass band filtering in the frequency range of 8-55 Hz. We implemented this filter using a Fast Fourier Transform
2. Signal differentiation using a five point derivative (Pan and Tompkins, 1985) and pointwise squaring to enhance the R-waves and increase the signal to noise ratio
3. Temporal averaging of the differentiated and squared signal over 120 samples, corresponding to 120 ms for our sampling rate of 1 kHz.
4. Maximum search in the filtered ECG signal within a time window defined by discriminating the time-averaged signal against a fixed threshold defined as the mean value of the time-averaged signal plus 0.5 times its root-meansquare. The largest local maximum within each window was identified as an R-wave candidate.

5. To avoid potential erroneous detection/oversensing of T and P waves, a subsequent R-wave selection step was executed, comparing the running mean of the R-R distance ($\overline{RR}$) over the last 8 detected R-waves against the R-R distances (RR) between the current candidate (CND) and its predecessor (PRE) and successor (SUC), respectively. If the distance SUC-PRE <1.5 $\overline{RR}$ either SUC or CND were rejected, depending on which RR was in better agreement with $\overline{RR}$.

Figure 7:
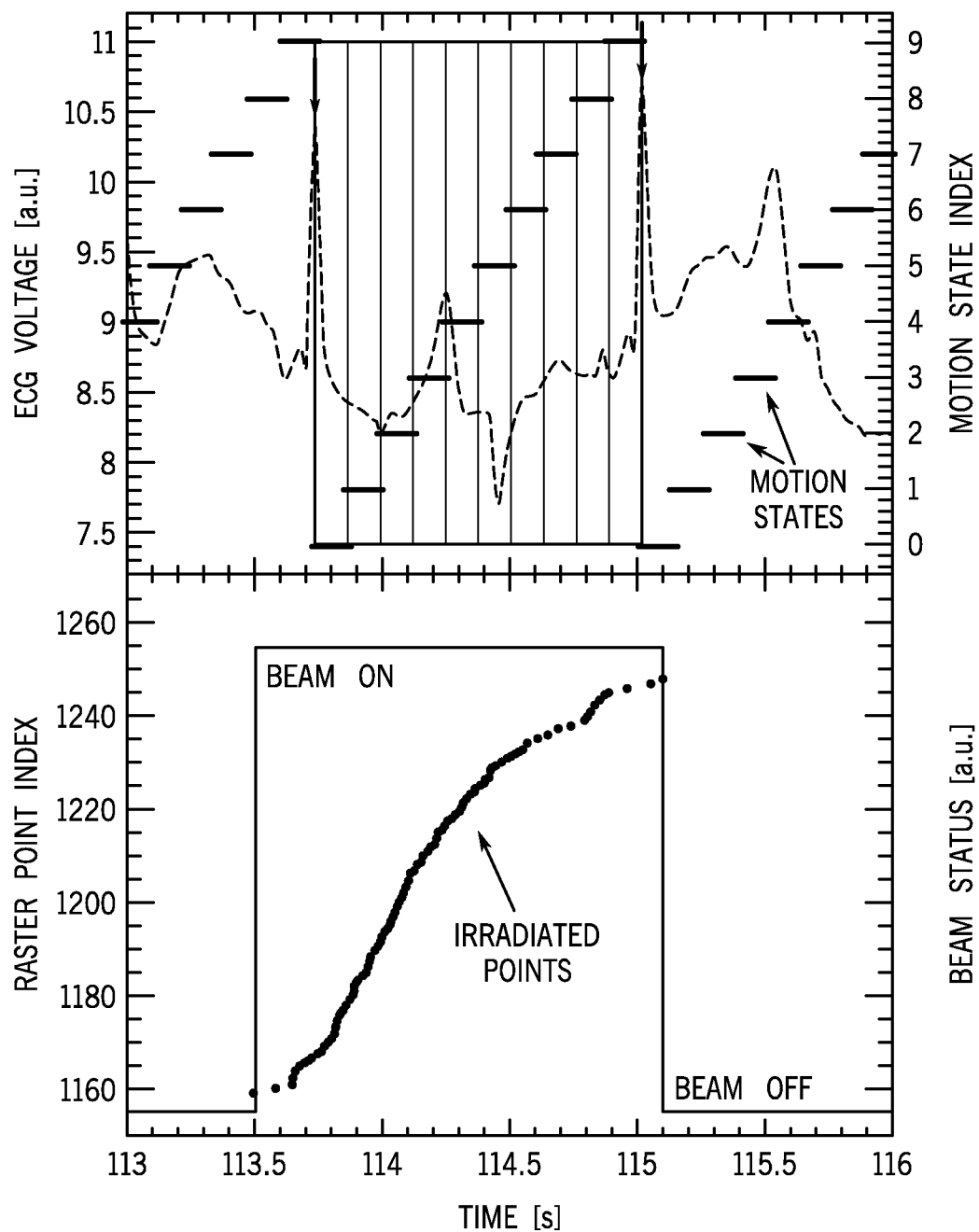
FIG. 7 shows that ECG signal processing yielded the position of the R-wave (red arrows) and served to equally distribute 10 motion states in time (grey boxes, green markers), in accordance with one or more non-limiting example embodiments. The lower panel shows the temporally correlated beam-on/off and raster point times.

In agreement with the algorithm used by the CT scanner during acquisition, motion states were then distributed over R-R distances in 10 equidistant steps and identified with the corresponding 4D-CT phases as illustrated in FIG. 7.

4D-dose calculation 4D-dose calculation was performed with the 4D treatment simulation functionality of TRiP4D. Details have been published elsewhere. Some of the steps uniquely applied in this study are briefly introduced here:

1. Mapping of each raster point to the respective 4D-CT phase based on the pre-processed ECG signal and the temporally correlated BDS as illustrated in FIG. 2. The mapping results into a 4D set of treatment plans, each containing raster points delivered in the respective 4D-CT phase.

2. 4D physical dose calculation based on the 4D treatment plan. Contributions to each dose voxel are accumulated on the reference 4D-CT phase by transforming the dose grid using the DIR vector fields and considering the changing densities of the 4D-CT.

Dose reconstruction was performed individually for each field. Total treatment dose distributions were subsequently formed by direct summation of the physical dose for both fields.

Data analysis: For each total dose distribution the mean dose ($D^-$) delivered to the TV, the volume receiving at least 95% of the planned dose (V95), and the homogeneity index HI=D5-D95 were assessed. D5 and D95 denote the dose received by 5% and 95% of the volume, respectively. D95 was also analyzed independently to determine the quality of dose coverage. For each OAR we report the mean dose ($D^-$) and the maximum point dose (Dmax).

Results: 4D-dose reconstructions were performed with TRiP4D via the custom developed GUI allowing efficient signal processing and data preparation. First calculations were conducted for single fields within about 30 min after treatment for some of the animals and allowed preliminary dose quality assurance. Results presented here were obtained from the final calculations conducted offline.

Observed cardiac motion from deformable image registration in the 4D-CTs was below 5 mm for all animals and targets, in line with motion described in men. Average amplitudes were 3.8 (range: 2.2-4.8) mm, 2.9 (1.8-3.9) mm, and 2.8 (1.8-4.4) mm, for the AV, PV, and LV target groups, respectively. Total irradiation times per field including respiratory gating were 9-21 min.

Figure 8:
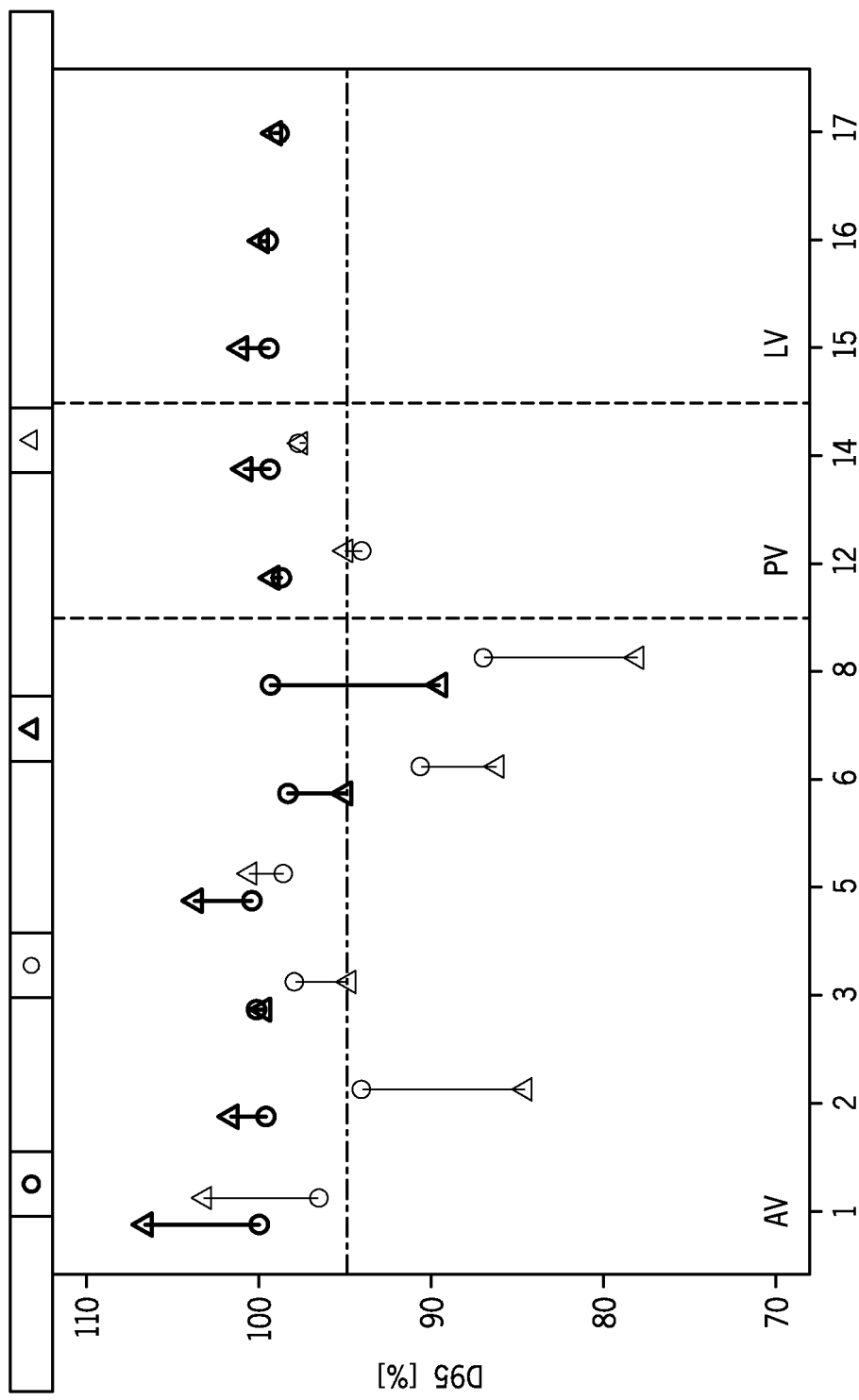
FIG. 8 shows planned and reconstructed 4D-dose reported as D95 in TV and PTV for each animal, in accordance with one or more non-limiting example embodiments. Values are relative to the different target doses for each animal (see also Table 3).
Figure 9:
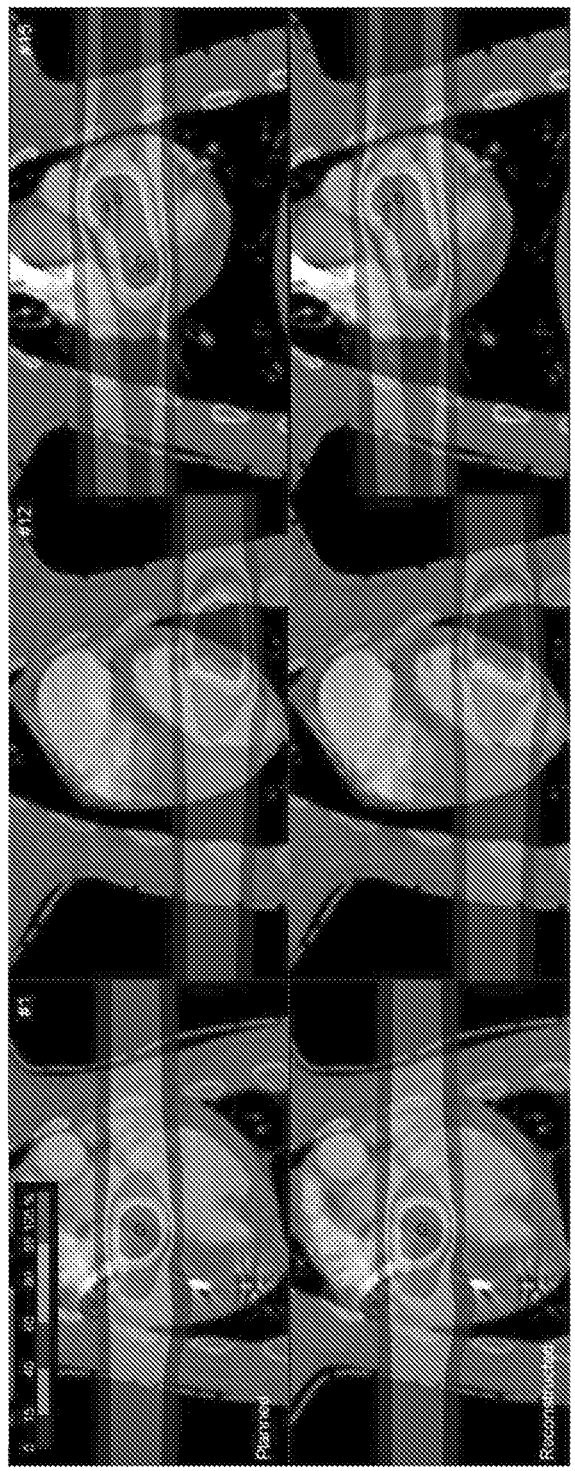
FIG. 9 shows dose cuts of the planned (top row) and reconstructed (bottom) 4D-dose for animals from the three different target groups AV (#1), LV (#12), and PV (#15) from left to right, in accordance with one or more non-limiting example embodiments. The dose is overlaid on the CE 4D-CT reference phase for better visibility of anatomic structures, but was calculated on the native 4DCT.)

Target coverage: FIG. 8 shows the results for the reconstructed D95 values of the TV and PTV, respectively. FIG. 9 shows dose cuts for reconstructed and planned 4D-doses for animals from all target groups. TV D95 values were >95% for all but one animal. The lower value for animal #8 is caused by technical problems, leading to misdelivered raster points for part of the TV. For LV and PV targets, planned and reconstructed TV D95 were comparable, while for AV targets larger variation was observed. Deviations for PTV D95 were larger than for TV D95, in particular for animals #2, #6, and #8 irradiated at the AV. It should be noted that the planned 4D-dose already showed a reduced D95 for these animals in the PTV (data not shown). Table 4 lists reconstructed V95, HI and $\overline{D}$ for TV and PTV volumes for all animals. With the exception of pig #8, all animals exhibited TV V95 of about 100%. PTV coverage was slightly reduced for most animals; to a larger extent for several animals of the AV group. HI values in the PTV exhibit larger variability indicating increased dose inhomogeneity compared to the TV, in particular for AV targets. TV and PTV volumes both show a systematic increase in $\overline{D}$ by around 5% with respect to the static dose reconstruction at about 100% of the planned dose.

TABLE 4

Table 4: 4D-dose reconstruction results. Listed are the volumes receiving at least 95% of the planned dose (V95), the homogeneity index (HI) and the mean dose ($\overline{D}$) in the TV and PTV volumes, respectively. Asterisks mark identical values for PTV and TV results, due to the fact that no additional PTV margins were added for LV targets.

| animal | target | TV V95 [%] | HI [%] | $\overline{D}$ [%] | PTV V95 [%] | HI [%] | $\overline{D}$ [%] |
|---|---|---|---|---|---|---|---|
| 1  | AV | 100.0 | 4.7  | 109.0 | 100.0  | 7.0   | 107.0  |
| 2  | AV | 100.0 | 14.8 | 111.0 | 81.2   | 23.1  | 106.0  |
| 3  | AV | 100.0 | 9.6  | 104.0 | 94.8   | 17.6  | 103.0  |
| 5  | AV | 100.0 | 5.6  | 107.0 | 99.9   | 9.7   | 105.0  |
| 6  | AV | 98.0  | 5.6  | 97.8  | 64.1   | 16.0  | 95.6   |
| 8  | AV | 68.2  | 14.0 | 97.0  | 63.1   | 28.5  | 95.8   |
| 12 | PV | 100.0 | 9.8  | 104.0 | 95.0   | 12.9  | 102.0  |
| 14 | PV | 100.0 | 7.6  | 105.0 | 98.3   | 10.4  | 103.0  |
| 15 | LV | 100.0 | 8.4  | 105.0 | 100.0* | 8.4*  | 105.0* |
| 16 | LV | 100.0 | 8.0  | 104.0 | 100.0* | 8.0*  | 104.0* |
| 17 | LV | 100.0 | 11.5 | 105.0 | 100.0* | 11.5* | 105.0* |

Figure 10:
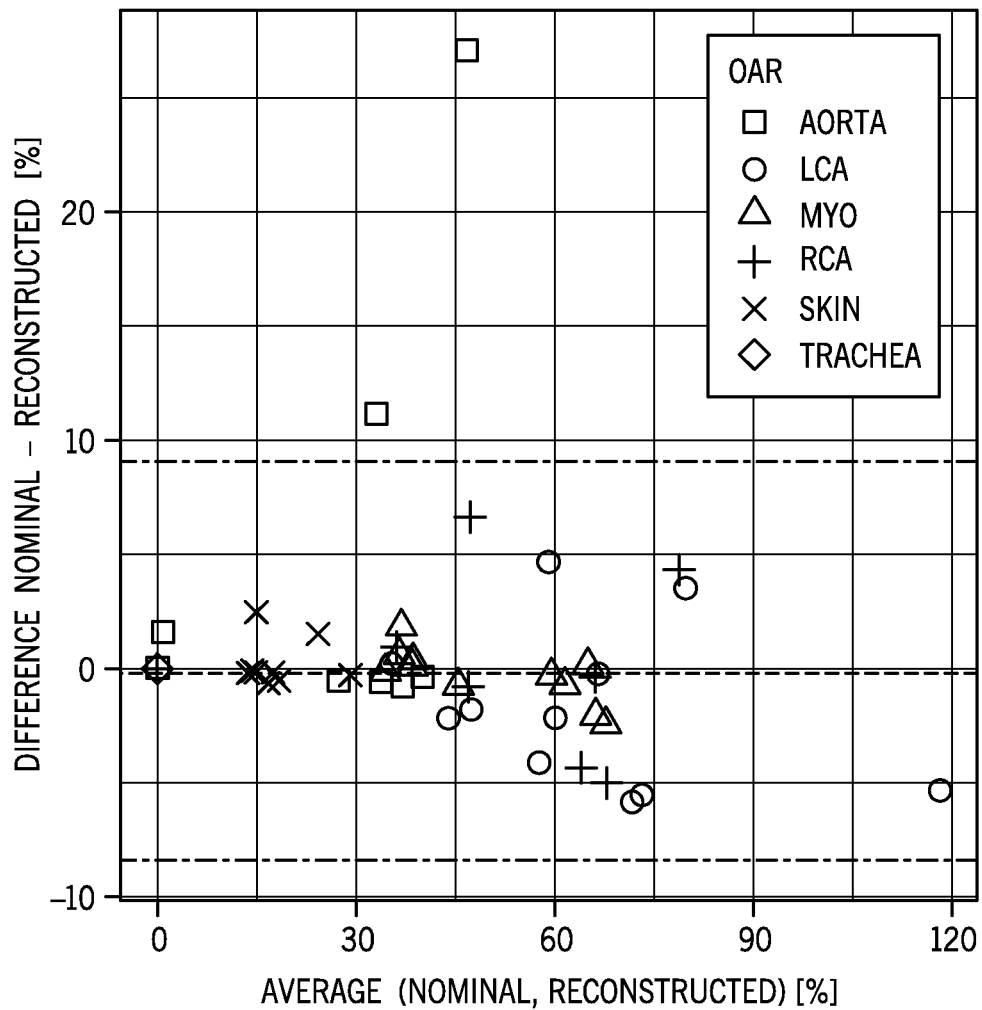
FIG. 10 shows a Bland-Altman plot comparing the 4D-nominal dose from treatment planning to the 4D-reconstructed dose, in accordance with one or more non-limiting example embodiments. Negative values indicate a higher dose in the reconstruction compared to planning. The dashed line indicates the median, the dash-dotted line the 95% confidence interval. Two animals received considerably lower dose to the ascending aorta in the reconstruction. The nominal dose is the average of all 96 motion scenarios considered per animal during treatment planning. All doses are reported relative to planning constraints.

Organs at risk: OAR exposure in comparison to the planned dose is reported in FIG. 10, relative to the planning dose constraints. The median difference was 0.1%, the standard deviation 4.5%. The two outliers receiving a lower dose were the ascending aorta, which was in close vicinity to the target in animals #3 and #8. The single over-dosed OAR is the LCA in #12, where the max point dose constraint of 30 Gy was already violated in treatment planning.

Discussion/Overview: In this study, we developed and successfully applied a 4D-dose reconstruction technique based on measured beam delivery sequences and for the first time for cardiac motion that was detected via a surface ECG surrogate. In contrast to previous applications of 4D-dose reconstruction, the workflow was improved so that preliminary data could be evaluated shortly after the irradiation. This permitted additional QA with respect to the irradiation of following animals. The reconstructed 4D-dose distributions showed acceptable target coverage (D95) for most of the treated animals, especially for LV-free wall and PV targets. The considerably smaller AV target volume showed reduced coverage of the PTV in some animals, and in retrospective data analysis also increased dose inhomogeneity throughout the TV and PTV volumes. This indicates that the applied rescanning approach could not fully mitigate interplay effects for the extremely small volumes and would have to be modified by, for instance, increasing the number of rescans, to provide increased robustness. To a smaller degree, also PV targets irradiated with IMPT showed a remaining impact of interplay (see Table 4).

Importance of respiratory motion suppression: Planning/compensating for respiration and cardiac motion is important for reducing side effects. In contrast to respiratory motion, where internal-external correlation mismatches and baseline drifts can be sources of substantial uncertainties, the impact of ECG variability on the reconstructed 4D-dose can be expected to be much smaller. Due to its physiological origin, the ECG and cardiac motion are highly correlated during normal sinus rythm. Therefore, with changes in heart rate covered by R-peak detection, the ECG could form an adequate surrogate for cardiac motion. Other methods to obtain a surrogate for heart motion can also be used, such as use of continuous wave radar to detect the heart rate and phase; advantages of this approach are that it does not require any instrumentation to be in contact with the patient's skin, and it results in absolute motion amplitudes. This approach can improve cardiac irradiations as it would make cardiac amplitudes available during irradiation. In another approach, heart and/or respiratory motion signals can be derived intrinsically from the raw data information at the CT reconstruction stage. This method could be combined with a surrogate available during irradiation to identify motion phases online.

4D-dose reconstruction: Online 4D-dose calculation is improved by implementing a GUI to optimize the 4D workflow. Using this GUI we could substantially accelerate the 4D-dose reconstruction workflow and obtain dose reconstruction results within minutes or hours instead of days. By reducing current limitations, such as manual data transfer, and further accelerating data processing and dose calculation, 4D-dose reconstructions can be performed immediately after treatment to obtain results within a few minutes. The improvements of our method are by no means limited to cardiac treatments but can readily be applied, for example, for treatments of patients with cancer disease as well as for 4D phantom measurements, e.g., for plan verification.

In the implementation of this study, the reconstruction workflow is the acquisition and processing of a surface ECG signal in contrast of a breathing trace. R-wave detection enabled to obtain the respective ECG phase which could be correlated to the cardiac 4D-CT phase (see FIG. 7). Since our 4DTPS is capable of using the signal phase to generate a 4D treatment plan, no adjustments were required from the TPS side. However, if both respiratory and cardiac motion are present, a more general approach may be used. If a 4D-CT is acquired such that it provides all N cardiac phases for each of the M respiratory phases, i.e. it has K=N×M phases, the current 4D-CT phase can be determined using the combination of a respiratory and an ECG surrogate and mapping the two dimensional phase index (n, m) to a one dimensional one: (n, m)→k=1 . . . K.

In this way 4D-dose reconstruction for mixed organ motion can be performed for a K phase 4DCT without changes to the 4D-dose calculation algorithm in our TPS. However, it should be noted that image registration is required for mapping all K phases to a single reference phase in certain implementations. Such an approach could be used to either treat free-breathing patients, or to include breath-hold variability in a simulation study or dose reconstruction, provided that appropriate images are available.

Improved image guidance for more precise dose reconstruction: In certain configurations, application of cone-beam CT (CBCT) or online MRI could substantially reduce positioning uncertainties, due to improved soft tissue contrast. In other configurations, online MRI could offer both excellent soft tissue identification and possibly also time-resolved targeting options, provided that MR image formation can be achieved at sufficient speed, image quality and resolution.

This study thus demonstrates surface-ECG based 4D-dose reconstruction for scanned ion beam treatment of electrophysiological target sites in the beating heart in a setting similar to clinical patient treatments. Estimation of the 4D delivered dose can contribute to ensure safe treatment of cardiac structures and is a helpful tool for dose verification. Beyond treatment of cardiac arrhythmia, also ion beam treatment of moving targets in radiotherapy of cancer diseases will benefit from these improvements as well.

As suggested, focused photonic therapy could be used in Langendorff preparations and in situ to ablate the AV node without use of catheters. This has been extended further in AV nodes, atrial tissue, and ventricular myocardium in intact pigs, with hadron therapy delivered in pencil beam formats to destroy arrhythmogenic tissue without using catheters. It is noted, however, that the linear accelerator based system is not restricted to the above applications as well. This approach could be used in such diverse applications as targeting of renal arteries to treat hypertension, treatment of seizures, treatment of occluded cardiac holes, noninvasive treatment of gastrointestinal maladies, modulation of nerve fibers, etc. For noncardiac applications, contouring may be site specific such that, for example, for the perirenal nerves, we may not need contouring of contractile motion but intraabdominal respiratory gating, descending aorta pulsations, other arterial pulsations, and ureteric and renal pelvis peristalsis.

Multiple, independently motile organs and structures may exist in close proximity. For the cardiac ventricular chambers and systemic arterial systems such as the aorta, descending aorta, iliac artery, carotid artery, etc., the electrocardiogram being used as a trigger with variable time offsets that increase with distance from the ventricles (greater time delay to the iliac artery compared to the ascending aorta, etc.) may be used to identify and track the movement of these structures. Contouring and modeling with the known geometry of the cylindrical aorta versus hemispherical aortic sinus of Valsalva, etc., may still be reliably approximated from knowledge of the onset of systole whose surrogate is the beginning of the QRS complex. On the other hand, venous, smooth muscle, and palatal muscle movement are not reliably predicted based on the electrocardiogram. For these, modification of both the method for tracking movement and the linear accelerator may be required for effective therapy. For instance, a simpler, smaller linear accelerator without sophisticated tracking and contouring may be used for structures such as the perinephric autonomic plexuses and nerves since movement of the kidney and its related vessels other than the renal artery which can be tracked as other arteries based on the cardiac cycle is minimal. However, in some instances, adequate knowledge of random skeletal muscle movement as well as peristaltic movement seen in smooth muscles including in the ureter and gastrointestinal tract may be essential for successful treatment of pathology around these structures. Here, a modification includes a vest or girdle placed on the patient so as to track in real time impedance and mechanical movements with contouring and tracking of large vessels from the ECG subtracted from these overall changes in three-dimensional impedance and mechanical movement. Based on this, sinuous peristaltic movement may be distinguished and related in depth to a structure in the region of projection known to produce such motility. Similarly, stimulating beams may be used to stimulate cerebral muscle and/or smooth muscle with resulting change in motion now being diagnosed to be from a particular structure with its own now identified as unique pattern in impedance change. Further modification of the linear accelerator to include an adjunctive, adjoined, or integrated ultrasound beam delivery device so as to mechanically stimulate or move sensitive structures wherein the beam is synchronized to particle beam delivery is an essential part of some applications of the present disclosure, for example, when a hiatal hernia has juxtaposed itself and gastric/intestinal contents through the foramen of Bochdalek or the foramina of Morgagni, which are not uncommon gaps in the diaphragm that normally separate the heart from these structures capable of peristalsis and where failure to recognize and differentiate the mobility may result in serious complication when delivering energy for arrhythmogenic cardiac substrate not meant for the intestinal structures.

The present invention has been described in terms of one or more preferred embodiments, and it should be appreciated that many equivalents, alternatives, variations, additions, and modifications, aside from those expressly stated, and apart from combining the different features of the foregoing embodiments in varying ways, can be made and are within the scope of the invention. In the above description, a number of specific details, examples, and scenarios are set forth in order to provide a better understanding of the present disclosure. These examples and scenarios are provided for illustration, and are not intended to limit the disclosure in any way. The true scope of the invention will be defined by the claims included in this and any later-filed patent applications in the same family.

Those of ordinary skill in the art, with the included descriptions, will be able to implement appropriate functionality without undue experimentation. References in the specification to an "embodiment," an "example," a "version," an "implementation," a "configuration," an "instance," an "iteration," etc., indicate that the embodiment, example, version, etc. described may include one or more particular features, structures, or characteristics, but not every embodiment, example, version, etc. necessarily incorporates the particular features, structures, or characteristics. Further, when a particular feature, structure, or characteristic is described in connection with an embodiment, it is believed to be within the knowledge of one skilled in the art to effect such feature, structure, or characteristic in connection with other embodiments whether or not explicitly indicated.

The computerized functionality described above may be implemented in hardware, firmware, software, single integrated devices, multiple devices in wired or wireless communication, or any combination thereof. Computerized functions may be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory. In the drawings, specific arrangements or orderings of schematic elements may be shown for ease of description. However, the specific ordering or arrangement of such elements is not meant to imply that a particular order or sequence of processing, or separation of processes, is required in all embodiments. Further, some connections or relationships between elements may be simplified or not shown in the drawings so as not to obscure the disclosure. This disclosure is to be considered as exemplary and not restrictive in character, and all changes and modifications that come within the spirit of the disclosure are desired to be protected.

What is claimed is:

1. A method for delivering accelerated atomic particles at a targeted tissue of a subject, the method comprising mapping the targeted tissue to compensate for movements of the targeted tissue during delivery of the accelerated atomic particles, the movements resulting from respiratory and cardiac motion of the subject, wherein mapping the targeted tissue comprises identifying individual structures within the targeted tissue and tracking movement of the individual structures throughout a cardiac cycle.

2. The method of claim 1, wherein the method comprises using gating to compensate for the movements.

3. The method of claim 2, wherein contouring is used to follow critical targets in the targeted tissue through subsequent treatment cycles to better avoid non-targeted tissue surrounding the critical targets.

4. The method of claim 1, wherein mapping the targeted tissue comprises phase contouring.

5. The method of claim 4, wherein the phase contouring comprises pre-procedural imaging to obtain sequential images throughout a treatment cycle, and tagging structures based on characteristics of structures during movement in the treatment cycle.

6. The method of claim 5, wherein the phase contouring further comprises analyzing a treatment cycle using a template cycle.

7. The method of claim 4, wherein the phase contouring provides feedback information such that delivery of the accelerated atomic particles can be varied based on changes in the phase contouring.

8. The method of claim 1, further comprising delivering the accelerated atomic particles using multiple energy beams to enhance Bragg peak effects.

9. The method of claim 8, wherein a first beam of the multiple energy beams provides a low-dose delivery to induce perturbations in a contour of the targeted tissue at a site of application, and a second beam of the multiple energy beams is subsequently used to test for the site of application.

10. The method of claim 8, wherein a first beam of the multiple energy beams is used to stimulate the tissue, while a second beam of the multiple energy beams is used to ablate targeted tissue, wherein the first beam is used as an endpoint for energy delivery from the second beam.

11. The method of claim 8, wherein a stimulating beam of the multiple energy beams is used for titration of energy delivery.

12. The method of claim 11, further comprising using an injected sensor to detect collateral damage.

13. The method of claim 1, wherein the targeted tissue is mapped through successive at least one of cardiac cycles or respiratory cycles.

14. The method of claim 1, wherein the targeted tissue is mapped in real time during delivery of the accelerated atomic particles.

15. The method of claim 1, wherein the targeted tissue is mapped simultaneously and concurrently with delivery of the accelerated atomic particles to better focus energy delivery.

16. The method of claim 15, further comprising using percutaneous, pericardial, subdural, per venous, and per subcutaneous placement of electrodes such that mapping of targeted tissue and delivery of accelerated atomic particles occur concurrently with sensing and stimulation of the targeted tissue.

17. The method of claim 1, wherein the accelerated atomic particles are at least one of atoms or protons.

18. The method of claim 1, wherein the accelerated atomic particles are carbon atoms.

19. The method of claim 1, wherein the targeted tissue is treated using the accelerated atomic particles externally and non-invasively.

20. The method of claim 1, wherein the targeted tissue is a portion of the heart of the subject, and treated using the accelerated atomic particles externally and non-invasively.

21. The method of claim 1, wherein the targeted tissue is treated with the accelerated atomic particles in conjunction with at least one of injectable devices or injectable particles.

22. The method of claim 21, wherein the injectable devices are adjunctive catheters.

23. The method of claim 22, wherein the adjunctive catheters include circuitry and electromagnetic navigation to enhance cardiac registration.

24. The method of claim 23, wherein the targeted tissue is a portion of the brain of the subject, the portion being in close proximity to sensitive vasculature or conduction tissue.

25. The method of claim 1, further comprising using an adjunctive, adjoined, or integrated ultrasound beam delivery device to mechanically stimulate or move sensitive structures not to be targeted.

26. The method of claim 25, wherein delivery of an ultrasound beam using the ultrasound beam delivery device is synchronized with delivery of the accelerated atomic particles.

27. A system for delivering accelerated atomic particles at a targeted tissue of a subject, the system comprising a particle delivery device controlled by a computing device that is configured to map targeted tissue to compensate for movements of the targeted tissue during delivery of the accelerated atomic particles, the movements resulting from respiratory and cardiac motion of the subject, wherein the computing device maps the targeted tissue by identifying individual structures within the targeted tissue and tracking movement of the individual structures throughout a cardiac cycle.

28. The system of claim 27, wherein the computing device is configured to gate delivery of the accelerated atomic particles using the particle delivery device to compensate for the movements.

29. The system of claim 28, wherein contouring is used to follow critical targets in the targeted tissue through subsequent treatment cycles to better avoid non-targeted tissue surrounding the critical targets.

30. The system of claim 27, wherein mapping the targeted tissue comprises phase contouring.

31. The system of claim 30, wherein the phase contouring comprises using sequential images obtained throughout a treatment cycle pre-procedurally, and tagging structures based on characteristics of structures during movement in the treatment cycle.

32. The system of claim 31, wherein the phase contouring further comprises analyzing a treatment cycle using a template cycle.

33. The system of claim 30, wherein the phase contouring provides feedback information such that delivery of the accelerated atomic particles can be varied by the computing device based on changes in the phase contouring.

34. The system of claim 27, wherein the particle delivery device is configured to provide multiple energy beams, and the computing device is configured to enhance Bragg peak effects using the multiple energy beams.

35. The system of claim 34, wherein the computing device is configured to provide a first beam of the multiple energy beams as a low-dose delivery to induce perturbations in a contour of the targeted tissue at a site of application, and deliver a second beam of the multiple energy beams that is subsequently used to test for the site of application.

36. The system of claim 34, wherein the computing device is configured to use a first beam of the multiple energy beams to stimulate the tissue, and a second beam of the multiple energy beams to ablate targeted tissue, wherein the first beam is used as an endpoint for energy delivery from the second beam.

37. The system of claim 34, wherein the computing device is configured to use a stimulating beam of the multiple energy beams for titration of energy delivery.

38. The system of claim 37, wherein the computing device is further configured to receive data from an injected sensor configured to detect collateral damage.

39. The system of claim 27, wherein the targeted tissue is mapped through successive at least one of cardiac cycles or respiratory cycles.

40. The system of claim 27, wherein the targeted tissue is mapped in real time during delivery of the accelerated atomic particles.

41. The system of claim 27, wherein the targeted tissue is mapped simultaneously and concurrently with delivery of the accelerated atomic particles to better focus energy delivery.

42. The system of claim 41, the computing device further configured to control percutaneous, pericardial, subdural, per venous, and per subcutaneous electrodes such that mapping of targeted tissue and delivery of the accelerated atomic particles occur concurrently with sensing and stimulation of the targeted tissue.

43. The system of claim 27, wherein the accelerated atomic particles are at least one of atoms or protons.

44. The system of claim 27, wherein the accelerated atomic particles are carbon atoms.

45. The system of claim 27, wherein the system is configured to use the accelerated atomic particles to treat the targeted tissue externally and non-invasively.

46. The system of claim 27, wherein the system is configured to use the accelerated atomic particles to treat a portion of the heart of the subject externally and non-invasively.

47. The system of claim 27, wherein the computing device is configured to treat targeted tissue with the accelerated atomic particles in conjunction with at least one of injectable devices or injectable particles.

48. The system of claim 47, wherein the injectable devices are adjunctive catheters.

49. The system of claim 48, wherein the adjunctive catheters include circuitry and electromagnetic navigation to enhance cardiac registration.

50. The system of claim 49, wherein the targeted tissue is a portion of the brain of the subject, the portion being in close proximity to sensitive vasculature or conduction tissue.

51. The system of claim 27, the computing device further configured to use an adjunctive, adjoined, or integrated ultrasound beam delivery device to mechanically stimulate or move sensitive structures not to be targeted.

52. The system of claim 51, wherein the computing device is configured to synchronize delivery of an ultrasound beam using the ultrasound beam delivery device with particle beam delivery using the particle delivery device.

* * * * *